US012805955B2

(12) United States Patent
Simi et al.

(10) Patent No.: US 12,805,955 B2
(45) Date of Patent: Nov. 24, 2026

(54) MASTER CONSOLE FOR ROBOTIC SURGERY

(71) Applicant: MEDICAL MICROINSTRUMENTS, INC., Wilmington, DE (US)

(72) Inventors: Massimiliano Simi, Calci (IT); Giuseppe Maria Prisco, Calci (IT)

(73) Assignee: MEDICAL MICROINSTRUMENTS, INC., Wilmington, DE (US)

( * ) Notice: Subject to any disclaimer, the term of this patent is extended or adjusted under 35 U.S.C. 154(b) by 797 days.

(21) Appl. No.: 17/056,341

(22) PCT Filed: May 17, 2019

(86) PCT No.: PCT/IB2019/054099
§ 371 (c)(1),
(2) Date: Nov. 17, 2020

(87) PCT Pub. No.: WO2019/220409
PCT Pub. Date: Nov. 21, 2019

(65) Prior Publication Data

US 2021/0205039 A1 Jul. 8, 2021

(30) Foreign Application Priority Data

May 17, 2018 (IT) ........................ 102018000005471

(51) Int. Cl.
*A61B 34/20* (2016.01)
*A61B 34/00* (2016.01)
(Continued)

(52) U.S. Cl.
CPC .............. *A61B 34/37* (2016.02); *A61B 34/20* (2016.02); *A61B 34/74* (2016.02); *A61B 46/10* (2016.02);
(Continued)

(58) Field of Classification Search
None
See application file for complete search history.

(56) References Cited

U.S. PATENT DOCUMENTS

| | | | |
|---|---|---|---|
| 3,338,626 A | 8/1967 | Hamilton | |
| 7,789,875 B2 * | 9/2010 | Brock | ................ A61B 17/0469 606/1 |

(Continued)

FOREIGN PATENT DOCUMENTS

| | | |
|---|---|---|
| CN | 106963499 A | 7/2017 |
| CN | 107049523 A | 8/2017 |

(Continued)

OTHER PUBLICATIONS

International Search Report and Written Opinion of the International Searching Authority for International Patent Application No. PCT/IB2019/054099 mailed Jul. 4, 2019, 14 pages.

(Continued)

*Primary Examiner* — Shahdeep Mohammed
(74) *Attorney, Agent, or Firm* — Merchant & Gould P.C.

(57) ABSTRACT

A sterile console includes at least one master input tool mechanically ungrounded and suitable to be hand-held by a surgeon during surgery. A surgical chair has a seating surface to accommodate the surgeon during surgery. A tracking system detects position and orientation of the master input tool within a predefined tracking volume. A tool supporting element receives the master input tool. The consoles also includes a slave robot assembly has at least one surgical instrument designed to operate on a patient anatomy, and a control unit. A field generator of the tracking system is integral with a portion of the surgical chair so that, when the surgeon is seated and hand-holds the master input tool, the master input tool is located within the predefined tracking (Continued)

volume. The position and orientation of the master input tool are detected by the tracking system.

17 Claims, 12 Drawing Sheets

(51) Int. Cl.

| | |
|---|---|
| ***A61B 34/37*** | (2016.01) |
| ***A61B 46/10*** | (2016.01) |
| ***A61B 90/60*** | (2016.01) |

(52) U.S. Cl.
CPC ...... *A61B 90/60* (2016.02); *A61B 2034/2046* (2016.02); *A61B 2034/2068* (2016.02)

(56) References Cited

U.S. PATENT DOCUMENTS

| | | | | |
|---|---|---|---|---|
| 10,561,370 | B2 | 2/2020 | Salazar | |
| 2004/0111183 | A1* | 6/2004 | Sutherland | A61B 34/76 700/245 |
| 2008/0177285 | A1 | 7/2008 | Brock et al. | |
| 2011/0238079 | A1* | 9/2011 | Hannaford | A61B 34/76 606/130 |
| 2013/0024024 | A1* | 1/2013 | Namiki | A61B 1/00149 700/245 |
| 2014/0018960 | A1 | 1/2014 | Itkowitz | |
| 2015/0045812 | A1* | 2/2015 | Seo | A61B 34/30 606/130 |
| 2016/0000515 | A1* | 1/2016 | Sela | A61B 34/10 600/424 |
| 2016/0331584 | A1 | 11/2016 | Ren | |
| 2018/0078034 | A1 | 3/2018 | Savall et al. | |
| 2018/0078319 | A1 | 3/2018 | Nobles et al. | |
| 2018/0092706 | A1 | 4/2018 | Anderson et al. | |
| 2018/0310886 | A1* | 11/2018 | Salazar | A61B 5/6891 |
| 2020/0170718 | A1* | 6/2020 | Peine | A61B 90/37 |

FOREIGN PATENT DOCUMENTS

| | | | |
|---|---|---|---|
| EP | 2 845 556 | A1 | 3/2015 |
| JP | 3051342 | * | 8/1998 |
| JP | 3051342 | U | 8/1998 |
| WO | 2014/151621 | A1 | 9/2014 |
| WO | 2016/201207 | A1 | 12/2016 |
| WO | 2017/064303 | A1 | 4/2017 |
| WO | 2017/064306 | A1 | 4/2017 |

OTHER PUBLICATIONS

Rotator Cuff Tear Pain and Tear Size and Scapulohumeral Rhythm, Journal of Athletic Training 2009; Jason S. Scibek, et al. ("Scibek"), 12 pgs.
The Use of Electromagnetic Motion Tracking Analysis to Objectively Measure Open Surgical Skill in the Laboratory-Based Model, J. Am. Coll. Surg., Published 2001, Datta, et al. ("Datta"), 7 pgs.
Third-Party Submission Under 37 CFR 1.290 Concise Description of Relevance submitted in U.S. Appl. No. 17/748,701, 25 pgs.

* cited by examiner

MASTER CONSOLE FOR ROBOTIC SURGERY

FIELD OF THE INVENTION

It is an object of the present invention a sterile console.

In particular, said sterile console is suitable for robotic surgery.

The present invention also relates to a robotic surgery system as well as an operating arena comprising said sterile console.

Further, it is an object of the present invention a method for performing surgery.

BACKGROUND

Robotic surgery assemblies comprising a master interface and a slave surgical tool are generally known in the art. Specifically, robotic surgery assemblies of the known type comprise a control station comprising a display and connected to the master interface, as shown for example in document WO-2016-201207, wherein an appendices of the control station acts as master input tool to control the slave surgical instrument operating on a patient anatomy.

For example, document US-2008-177285 shows a master console station equipped with armrests attached to a seating element, wherein from each armrest a mechanically constrained appendix protrudes forming a free end comprising a metallic wearable ring designed to fit over a surgeon's finger, to detect manual commands provided by the surgeon wearing such a ring. The master control appendix is directly connected to an articulated lever assembly to transmit a command to the slave part of the robot.

The surgical master control station disclosed in the above mentioned document forces the surgeon's arm and hands to have an uncomfortable posture of during surgery due to the encumber of such a wearable mechanical appendix.

For example, document EP-2845556 shows a master console station for remote robotic surgery equipped with a display and a control chair, said control chair comprising mechanical appendices protruding from a frame structure integral with the chair armrests, said mechanical appendices acting as master input tool to control a slave surgical robotic arm. Such master input appendices are connected to force/torque detectors and force compensators for detect the intended surgeon's manual command and to transmit such information to the slave surgical tool through a data processing unit.

This remote console station forces the surgeon to operate while seating in a dedicated control room as the remote console station is unsuitable to be sterilized and placed within the sterile operatory arena, i.e. around the operating table, and at the same time such a console station is designed to be unmovable, in other words is designed not to be easily relocated in various locations of the remote control room.

Moreover, such a remote console station forces the surgeon to operate inserting his/her arms within a metallic frame to access the master control appendices. Although satisfactory in reducing the noise mainly due to mechanical vibration transmittal from the surgeon to the master mechanical appendices provided with force/torque detectors, this solution forces the surgeon to operate while assuming an uncomfortable position and posture, particularly during long-lasting surgical operations. While using such a remote console station to perform robotic surgery, the surgeon's perception of the surgery is unrealistic, as surgeon seats in a unmovable console placed in a room that ideally can be located far away from the operating arena and handles master control appendices provided with force/torque detectors and having the appearance of control levers.

Is therefore felt the need to improve the surgeon's comfort during robotic surgery and at the same time to make the surgeon in condition to handle familiar master controllers.

For example, documents WO-2017-064303 and WO-2017-064306, in the name of the same Applicant, show a master interface having a control tool which replicates the aspect of a pair of ordinary surgical tweezers, these tweezers being equipped with sensors to suitably detect a tracking field generated by a tablet, connected to the tweezers. Although partially satisfactory and specifically for shortening the surgeon's training period for performing robotic surgery due to the familiarity of handling such pair of ordinary surgical tweezers, these solutions are prone to drawbacks.

In particular, in such known solutions, the volume detected by the tracking tablet is restricted to a portion of the space located above the tracking tablet. Therefore, the surgeon is not allowed to move the master input tool below master tracking tablet, limiting the range of motion of the surgeon during operation and its comfort as well. In other words, as the surgeon moves the master controller below master tracking tablet, the latter is unable to detect the motion of the master controller and to accordingly transmit the motion to the slave robotic end effector.

Therefore, the need is felt to improve the freedom of movements of the surgeon during robotic surgery and at the same time to make the surgeon in condition to handle familiar master controllers.

Document US-2014-0018960 discloses a master interface comprising a remote console linked to a control system for actuating a tele-operated slave robotic arm operating on a patient. The console is equipped with a mechanically ungrounded master tool grip device defining a body-centric frame of reference, in other words a frame of reference centered on the surgeon handling such a mechanically unconstrained master tool grip device. In that way, that the control unit detecting the body-centric frame of reference acquires information about position and orientation of said master tool grip device and send a command signal to the slave robot arm to actuate the end-effector thereto. Other examples of remote console are shown in documents US-2018-0078319 and US-2018-0092706.

A solution for laparoscopic surgery is known from document WO-2014-151621 showing a master platform comprising a display, suitable to show the laparoscopic view, a wired or wireless master controller optically- or electromagnetically-tracked, and a resting bar suitable for the standing surgeon's forearm to rest thereon. Main advantage of this solution is the capability of tracking the motion of the master controller in a volume extending both above and below the resting bar, resulting in an extended range of motion for the surgeon during laparoscopic surgery and allowing the surgeon to rest his forearm on said resting bar. Furthermore, such solution also allows the surgeon to simultaneously employ a master controller for operating through the end-effector of the robot together with a habitual surgical tool suitable to operate directly on a living anatomy, providing the surgeon with a wide range of possible surgical therapies.

Despite the advantage described above, the disclosed solution fails to provide the surgeon with a comfortable yet reliable posture during robotic surgery. Due to the inherent uncomfortable surgeon posture forced by this master platform solution, the optical tracking of the master controller disclosed herein permits the surgeon to walk around the operating arena during surgery, but that often result in a loss of focus by the surgeon and/or the surgical team, particularly for long-lasting operations, and as well unwanted accidental collisions with the robotic assembly can easily arise.

The need is felt to provide a sterile console solution for robotic surgery allowing the surgeon to operate while is in a comfortable posture and at the same time suitable to improve the safety of the patient and of the robot parts during robotic surgery.

The need is felt to provide a sterile console solution allowing the surgeon to safely operate while is in a comfortable posture, avoiding for that reason to limit the range of motion allowed.

The need is felt to provide a sterile console for robotic surgery suitable for improving the precision, the focus and therefore the reliability of robotic surgery and at the same time suitable for long-lasting operation, without for that reason resulting highly uncomfortable or unfamiliar for the surgeon.

Solution

It is a scope of the present invention to overcome the drawbacks mentioned with reference to the known art.

It is a scope of the present invention to provide a sterile console for robotic surgery system, designed to improve the comfort of the surgeon during robotic surgery, avoiding to result for that reason the reliability of robotic surgery.

These and other scopes are achieved by a sterile console according to claim 1, as well as a robotic surgery system according to claim 12, as well as a operating arena according to claim 14, as well as a method according to claim 16.

Some preferred embodiments are the subject of dependent claims.

According to an aspect of the invention, a sterile console for a robotic surgery system comprises at least one master input tool mechanically ungrounded and suitable to be hand-held by a surgeon during surgery, at least one surgical chair comprising at least one seating surface for the surgeon to seat thereon during surgery, at least one tracking system, suitable to detect position and orientation of said at least one master input tool within a predefined tracking volume, and at least one tool resting element providing a support for said at least one master input tool to rest thereon when the surgeon does not hand-hold said at least one master input tool.

Said at least one master input tool defines at least one first frame of reference attached thereto, and said tracking system comprising a field generator defines a second frame of reference attached thereto, and said tracking volume is integral with said field generator of the tracking system, and the position and orientation detected by said tracking system is the position and orientation of said at least one first frame of reference with respect of the second frame of reference, so that a control unit of the robotic surgery assembly is suitable for receiving information about said position and orientation of said at least one master input tool within said tracking volume and is suitable for transmitting a command signal to the slave robot assembly in order to actuate said at least one surgical instrument.

The field generator of the tracking system, for example a magnetic field generator, is integral with a portion of the surgical chair so that, when the surgeon seats onto said seating surface of the surgical chair and hand-holds said at least one master input tool, said master input tool is located within said tracking volume and the position and orientation thereof can be detected by the tracking system.

The seating surface of the surgical chair may pivot about a substantially vertical roll axis, and said field generator of the tracking system is integral with said seating surface so that that the tracking volume is integral with the seating surface of the surgical chair of the sterile console during pivoting of the seating surface around the substantially vertical roll axis.

The surgical chair may comprise a seating lower support portion integral with said seating surface and a chair base structure providing structural support to a seating lower portion and said seating lower support portion may pivot around a substantially vertical roll axis with respect of said seat base structure, and the field generator may be integral with said seating lower support portion, so that the tracking volume is integral with the seating surface of the surgical chair of the sterile console during rolling around the substantially vertical roll axis.

The sterile console may comprise a sterile drape covering at least said seating surface of the surgical chair, and preferably covering also the armrest surfaces of the armrest assembly of the surgical chair, and preferably covering also the back seat portion of the surgical chair. The sterile drape may comprise a plastic lining or the like.

Thanks to the proposed solutions, it is provided a sterile console for robotic surgery suitable for being located within an operating arena surrounding a patient anatomy during surgery and suitable for being moved during surgery without for this reason resulting in the transmission of unwanted command signals to the surgical end effector.

An operating arena may comprise at least one of said sterile console, and at least one slave robot assembly comprising at least one surgical instrument designed to operate on a patient anatomy, and a patient supporting structure, for example an operatory bed or the like, forming a support for a patient anatomy to rest thereon during surgery and located within the operating arena.

The sterile console may be placed inside the operating arena near the operatory bed without for this reason requiring a single use only.

A robotic surgery system may comprise at least one of said sterile console and at least one slave robot assembly comprising at least one surgical instrument designed to operate on a patient anatomy, and a control unit, suitable for receiving information about said position and orientation of said at least one master input tool within said tracking volume and is suitable for transmitting a command signal to the slave robot assembly in order to actuate said at least one surgical instrument. The robotic surgery system in its entirety may be located within the operating arena.

FIGURES

Further characteristics and advantages of the invention will appear from the description reported below of preferred embodiments, which are given as examples and are not meant to be limiting, which makes reference to the attached figures, in which.

DETAILED DESCRIPTION OF PREFERRED EMBODIMENTS

Figure 1:
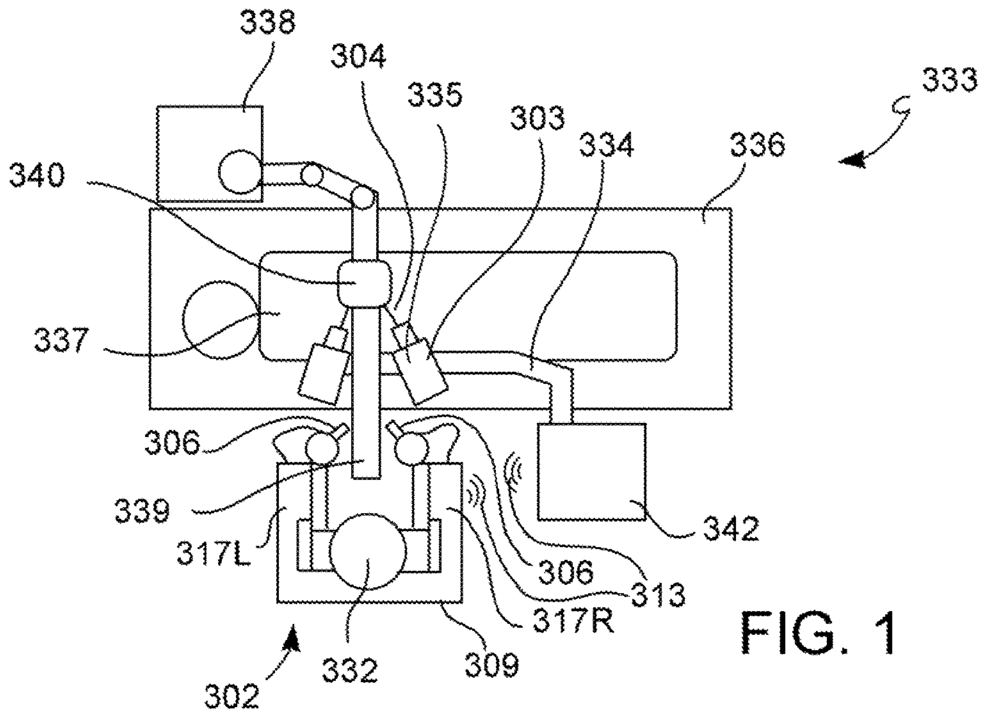
FIG. 1 is a top view showing diagrammatically a sterile console within an operating arena, according to an embodiment.

According to a general embodiment, a sterile console 302 for a robotic surgery system 301 is provided.

According to a general embodiment, a robotic surgery system 301 is provided comprising at least one of said sterile console 302.

According to a preferred embodiment, said robotic surgery system 301 comprises at least one master input tool 306.

Said master input tool 306 is mechanically ungrounded and suitable to be hand held by a surgeon 332. Preferably, with the terminology "mechanically ungrounded" master input tool 306 is intended a master input tool that is mechanically unconstrained with respect to possible position and orientation motion in a predefined working volume. For example, a predefined working volume is a volume that permits tracking of position motions within arm's length of the surgeon 332 and tracking all orientations.

According to an embodiment, said robotic surgery system 301 comprises said at least one sterile console 302, suitable to detect a manual command 348, and at least one slave robot assembly 303, wherein said sterile console 302 comprises said master input tool 306, and wherein said slave robot assembly 303 comprises at least one surgical instrument 304, designed to operate on a patient anatomy 337. Preferably, said at least one surgical instrument 304 forms a tele-operated end-effector of the slave robot assembly 303 paired along a master-slave pair with said master input tool 306.

According to an embodiment, said mechanically ungrounded master input tool 306 is unconstrained from the slave robot assembly 303 for both position and orientation motions within a surgeon's reachable workspace and/or a hand-tracking a transmitter's workspace (for example sway, heave, surge, pitch, yaw, and roll in a Cartesian coordinate system, and the like). Preferably, said master input tool 306 is an ungrounded master input tool.

According to a preferred embodiment, said at least one master input tool 306 is suitable to be hand-held and manipulated by a surgeon 332 from various locations of an operating arena 333 during surgery. According to a preferred embodiment, the terminology "operating arena" refers to a portion of space at least partially surrounding a patient anatomy 337. Preferably, within the operating arena 333 are comprised various locations beside the patient anatomy. Preferably, the terminology "operating arena 333" does exclude remote locations, such as remote consoles 358, in tele-communication with a surgical robot placed beside the patient anatomy, for examples comprising visualization screens. Preferably, the terminology "operating arena" refers to locations in the same room of the patient during surgery from where the surgeon may directly see the patient anatomy 337.

According to a preferred embodiment shown for example in FIG. 1, the sterile console 302 is located within the operating arena 333.

According to a preferred embodiment, said sterile console 302 comprises a sterile drape 361 covering said seating surface 310 of the surgical chair 309. Thanks to the provision of said sterile drape 361, a biological separation is provided from the seating surface 310 of the surgical chair 309 of the sterile console 302 and the patient anatomy 337, thereby reducing the risk of contamination. Furthermore, in this way the surgical chair 309 does not need to undertake sterilization before each surgery, and can be placed within the operating arena 333.

Figure 2:
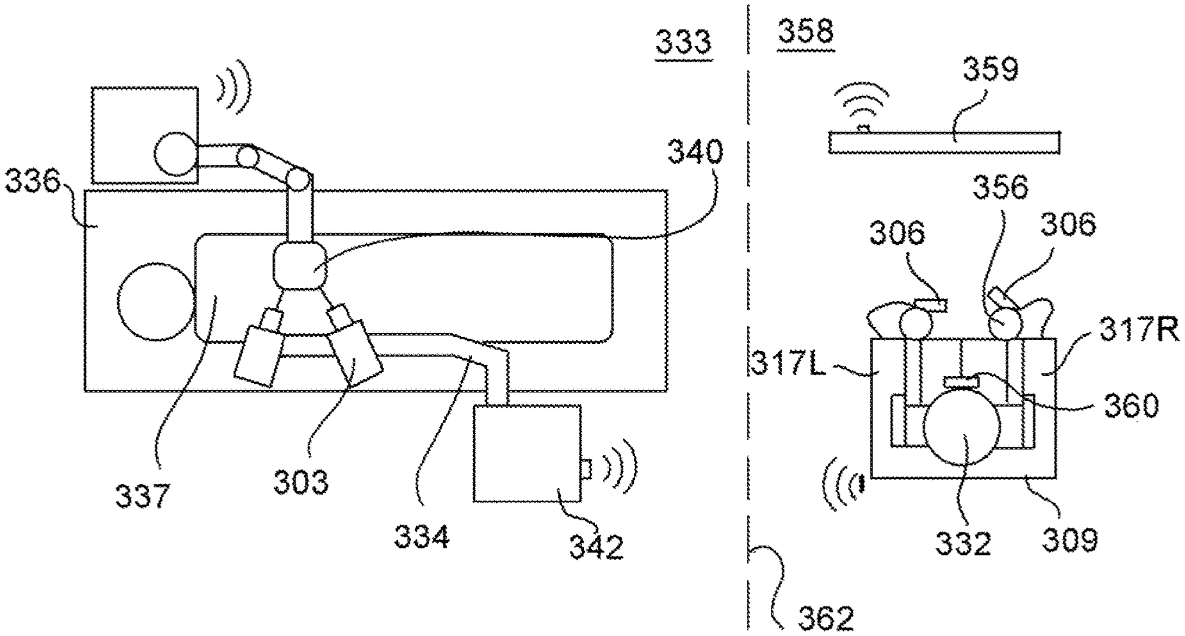
FIG. 2 is a top view showing diagrammatically a remote non-sterile console.
Figure 3:
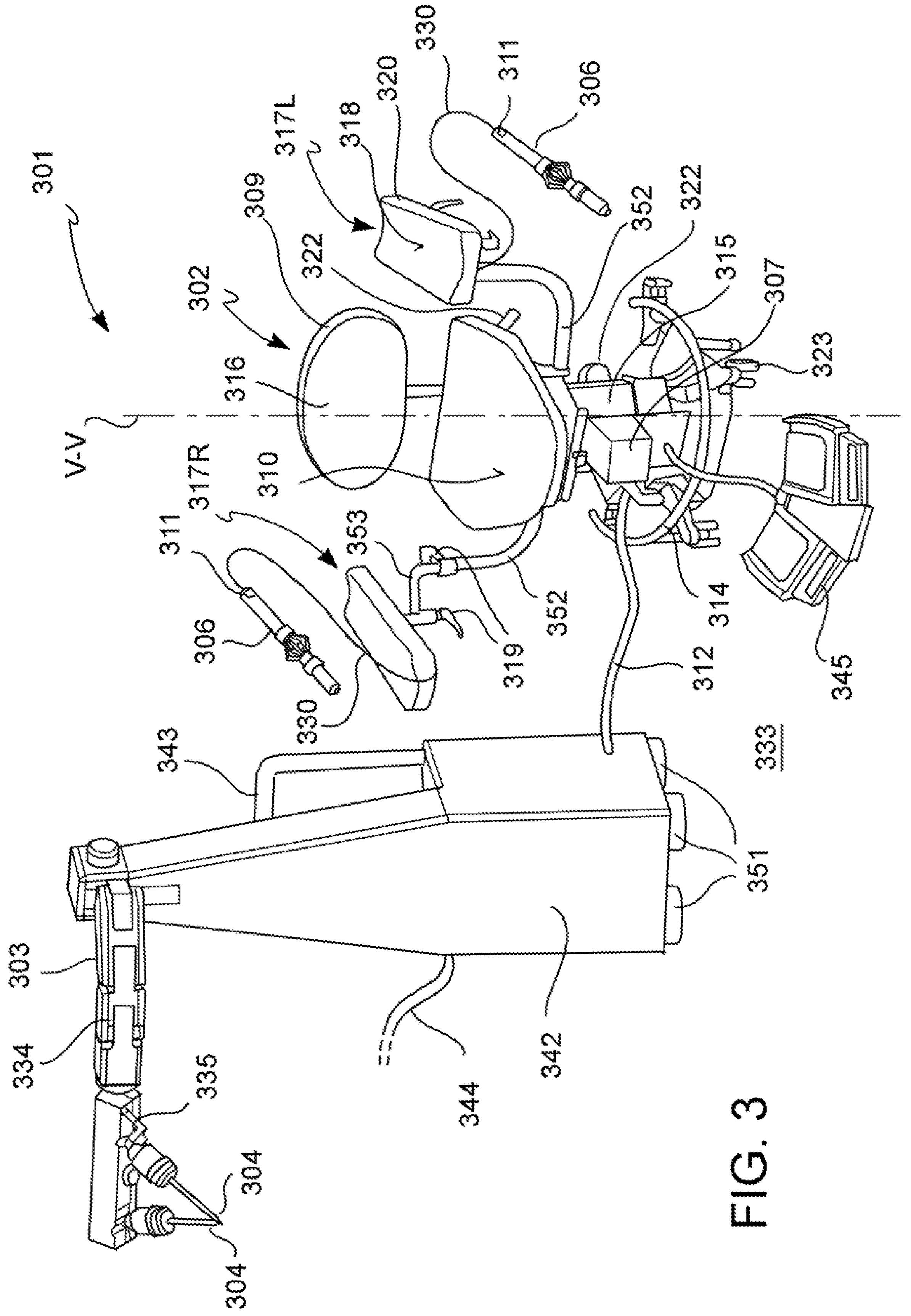
FIG. 3 is an axonometric view showing a robotic surgery system comprising a sterile console within an operating arena, according to an embodiment.
Figure 4:
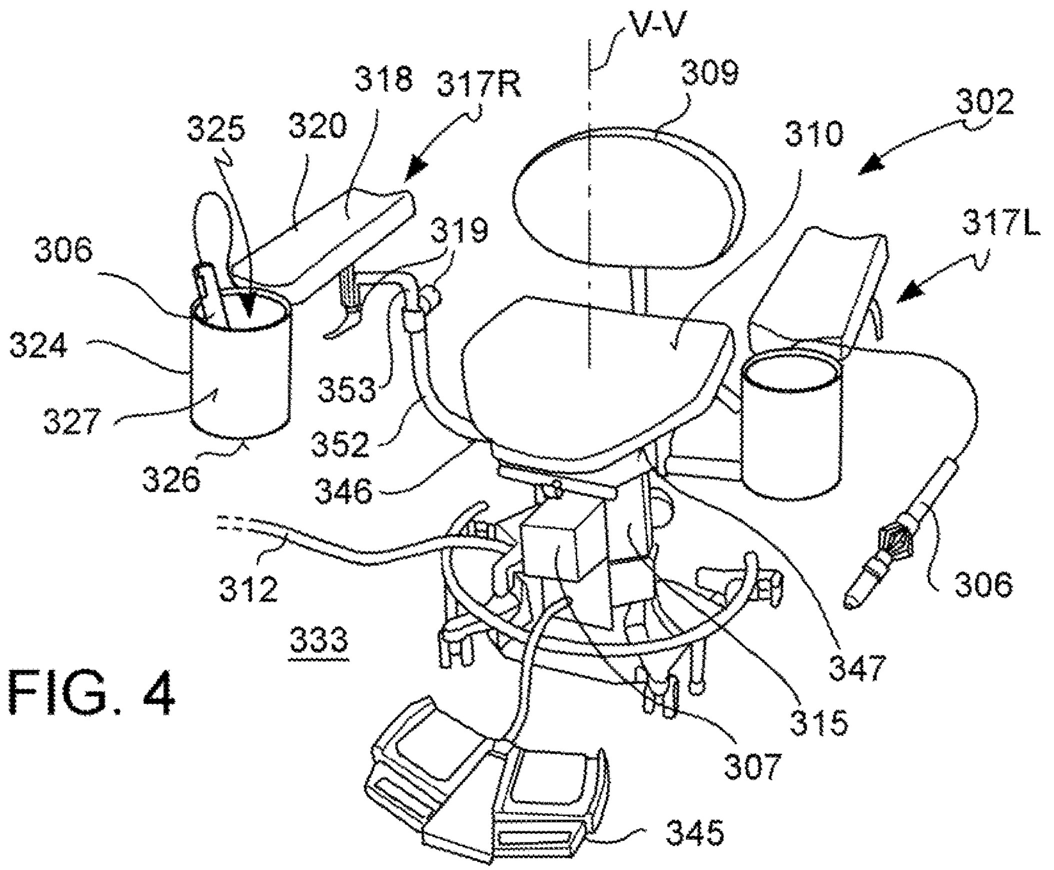
FIG. 4 is an axonometric view showing a sterile console, according to an embodiment.
Figure 5:
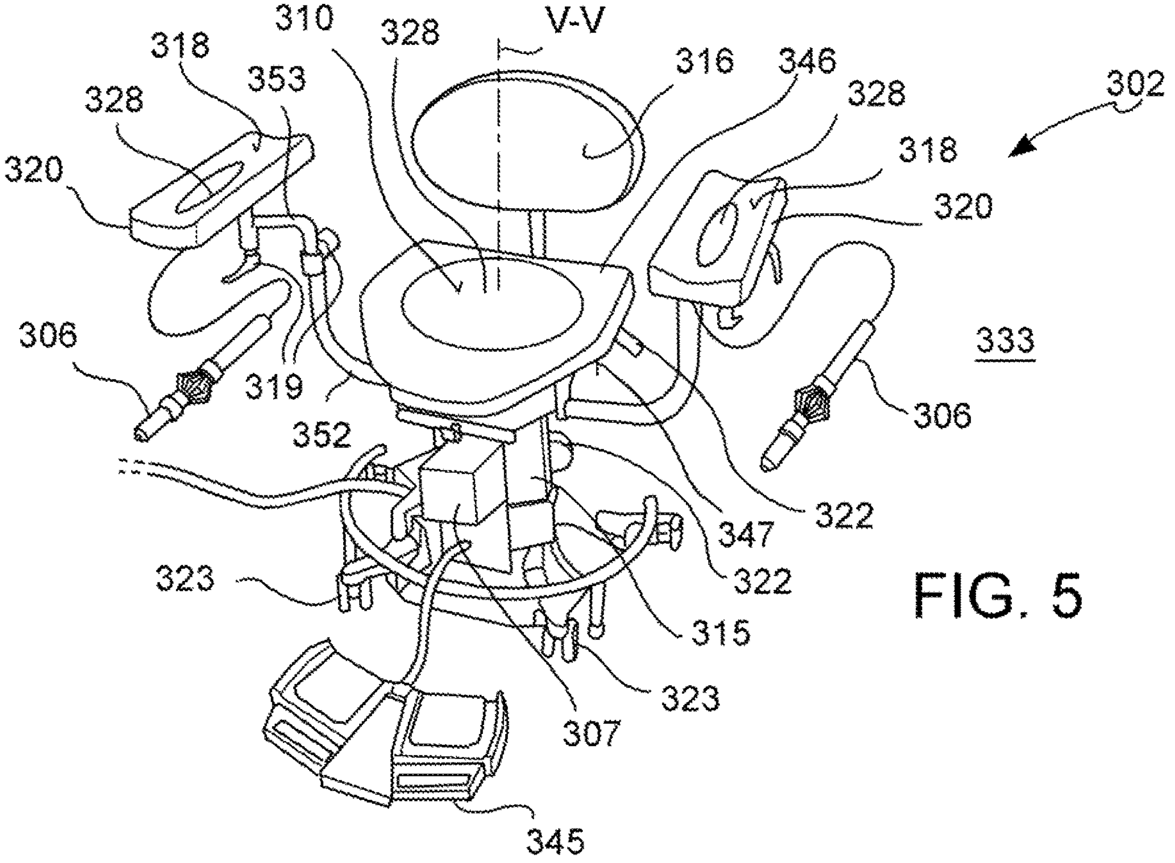
FIG. 5 is an axonometric view of a sterile console, according to an embodiment, wherein seating detector is shown.
Figure 6:
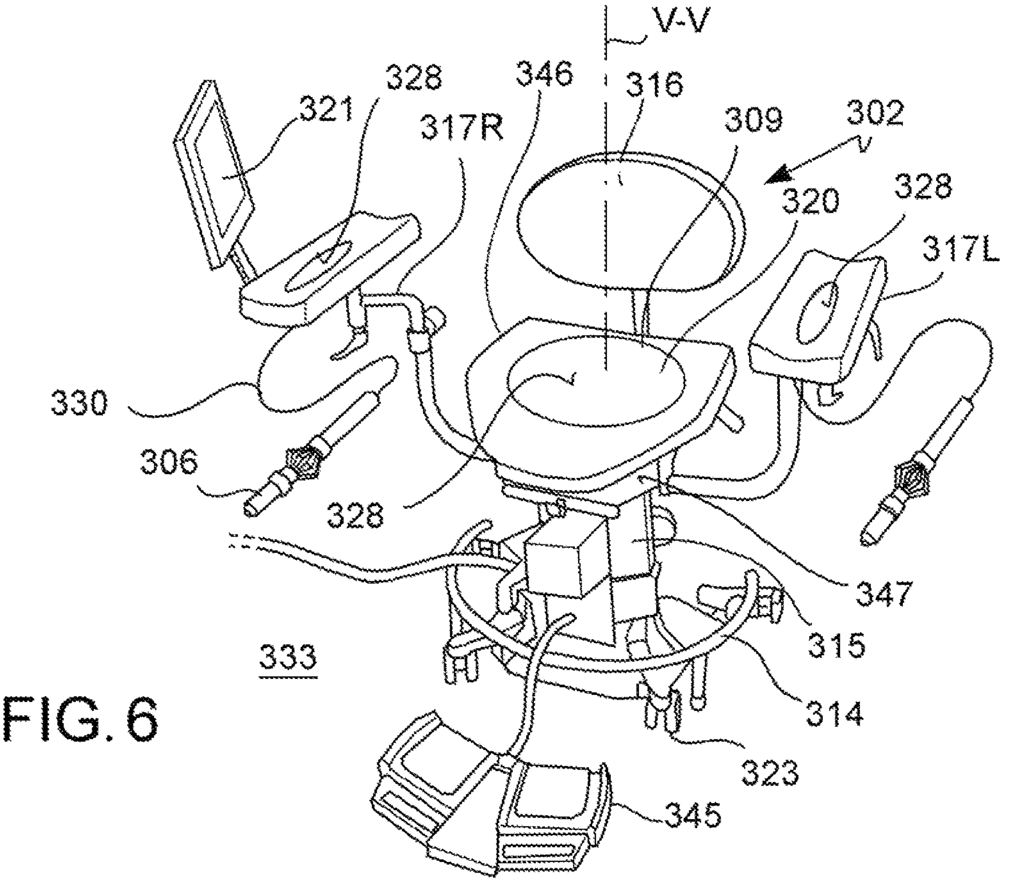
FIG. 6 is an axonometric view showing a sterile console, according to an embodiment, wherein seating detector and sterile display are shown.
Figure 7:
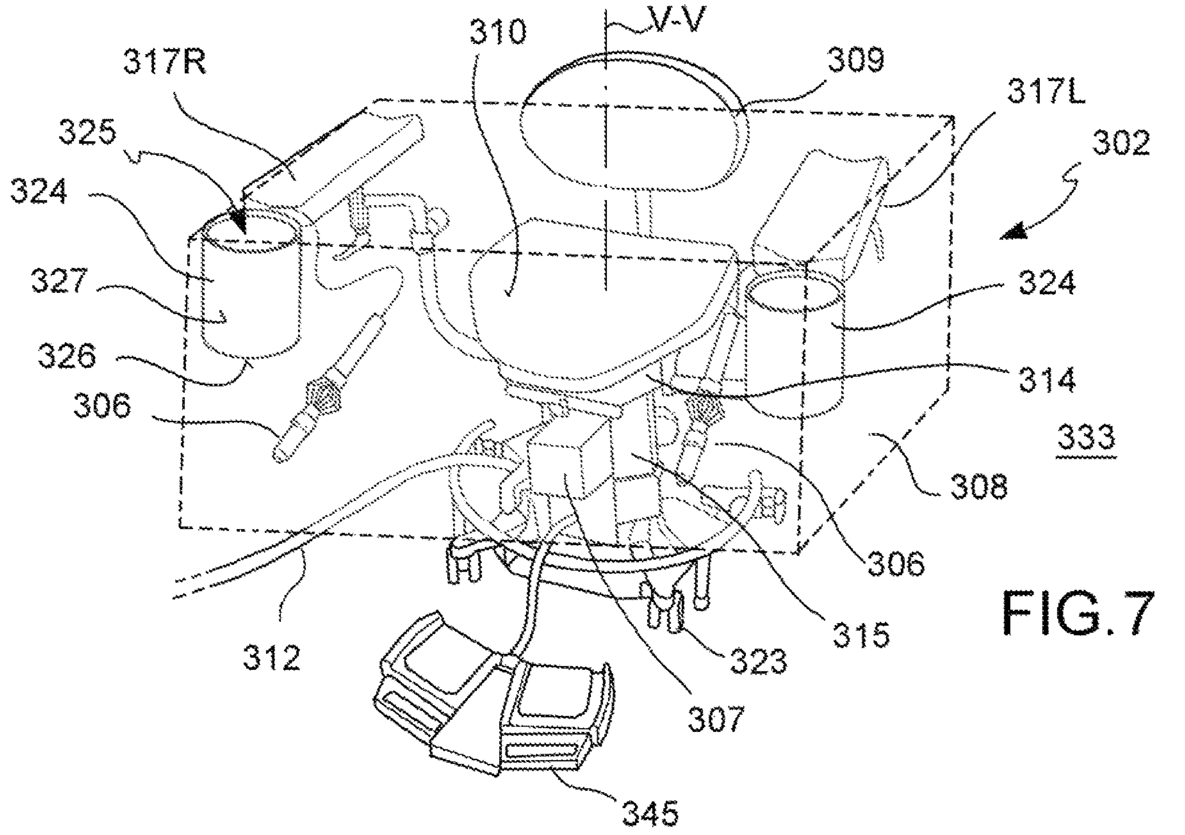
FIG. 7 is an axonometric view showing a sterile console, according to an embodiment, wherein predefined tracking volume is shown.
Figure 8:
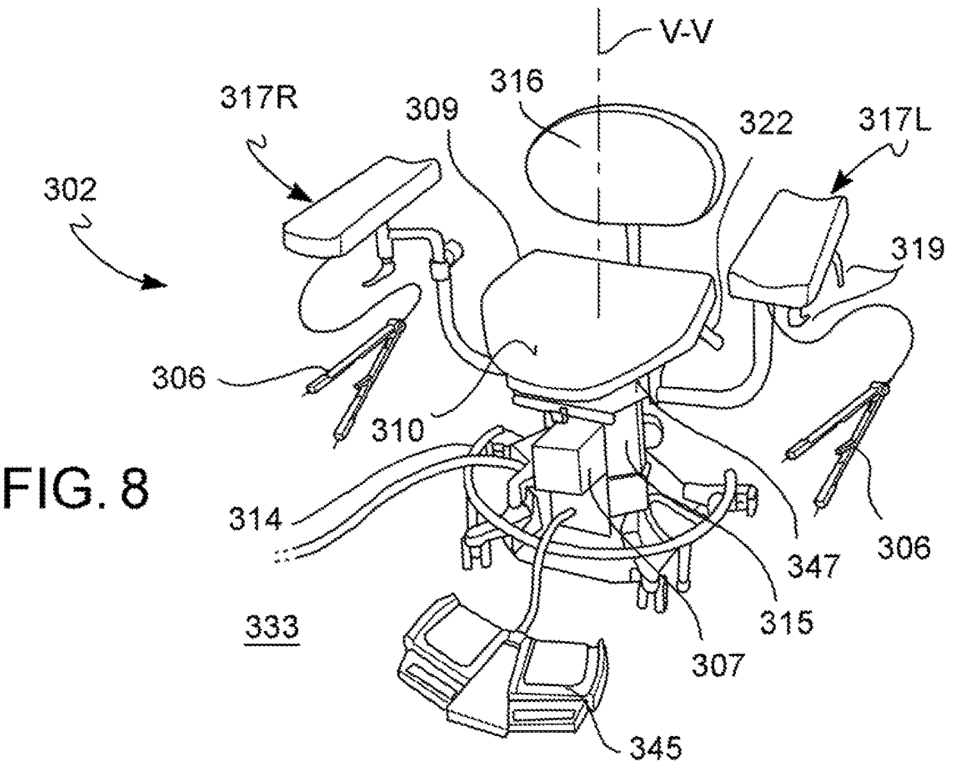
FIG. 8 is an axonometric view showing a sterile console, according to an embodiment.
Figure 9:
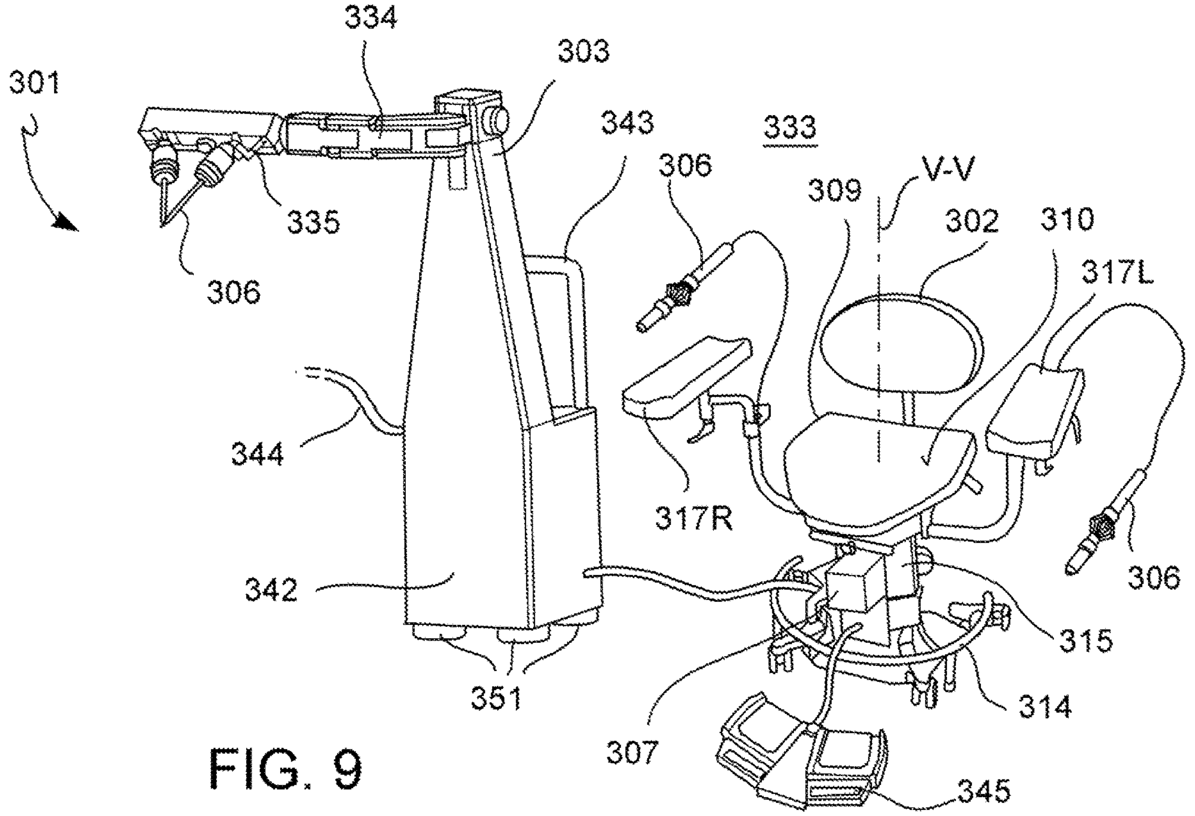
FIGS. 9 and 10 are axonometric views showing a robotic surgery system, according to some embodiments, comprising a sterile console.
Figure 10:
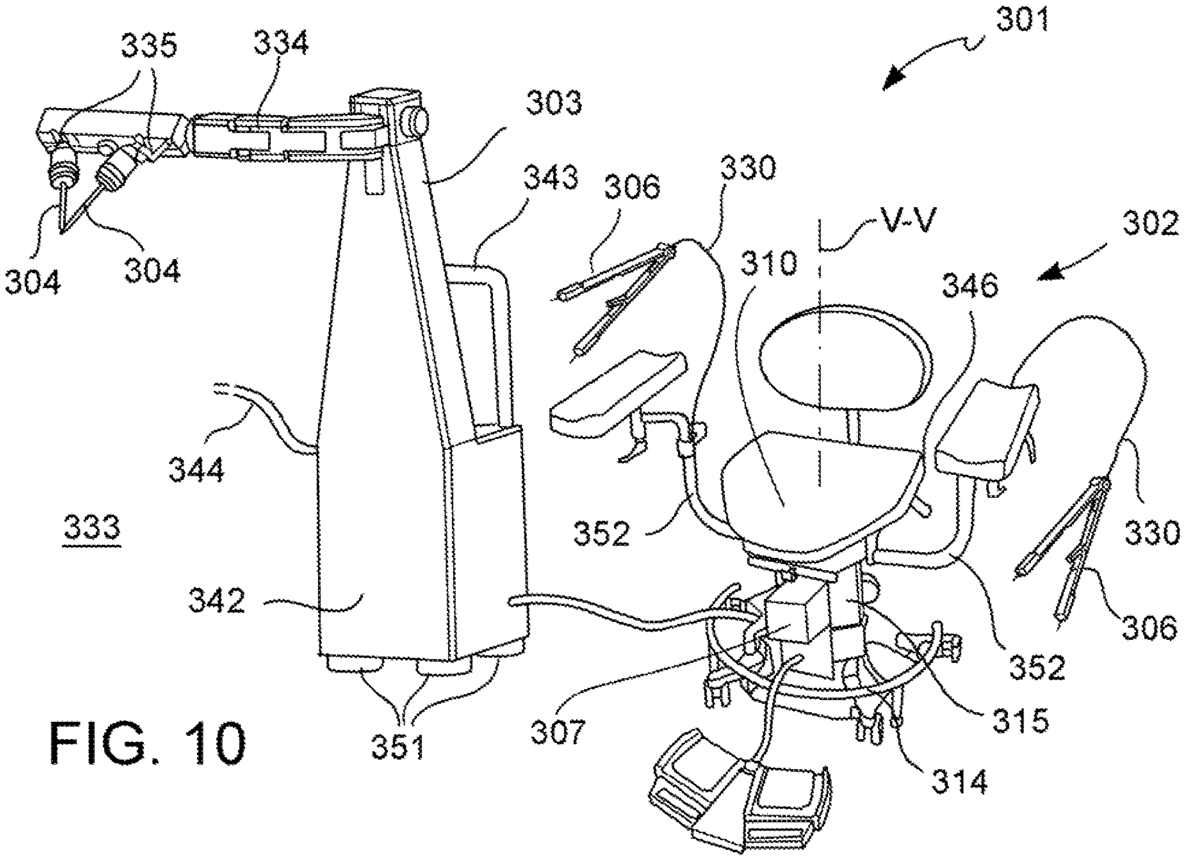
Figure 11:
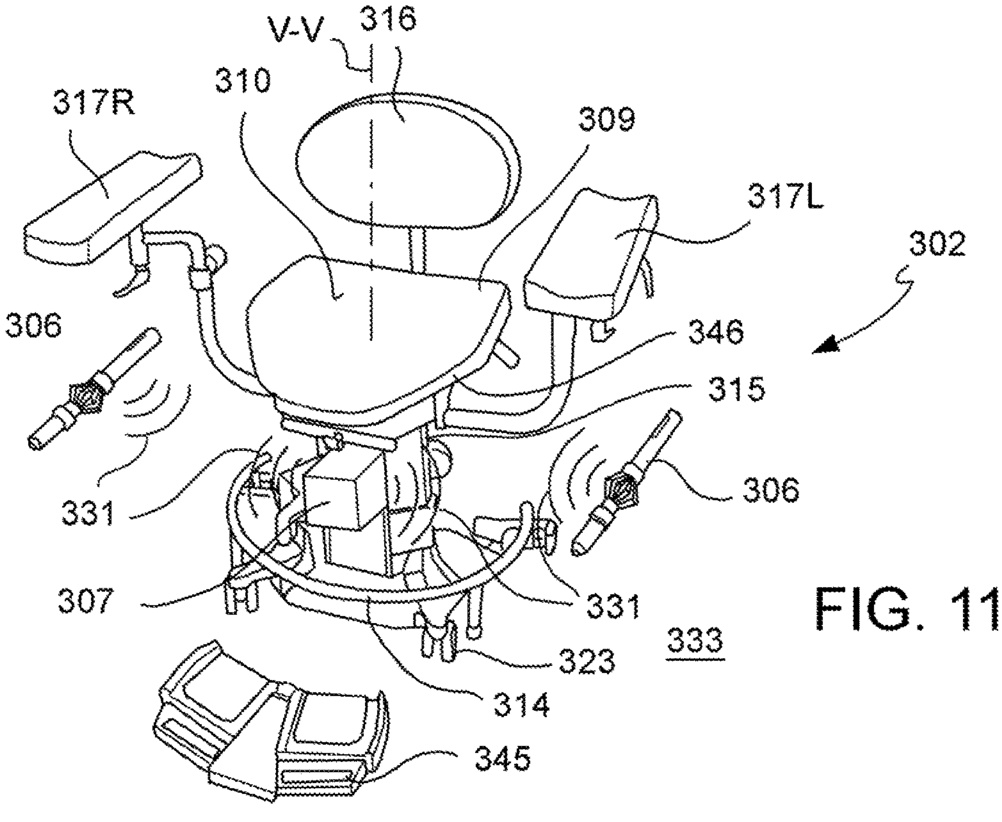
FIG. 11 is an axonometric view showing a sterile console tools, according to an embodiment, wherein tool wireless connection is shown.
Figure 12:
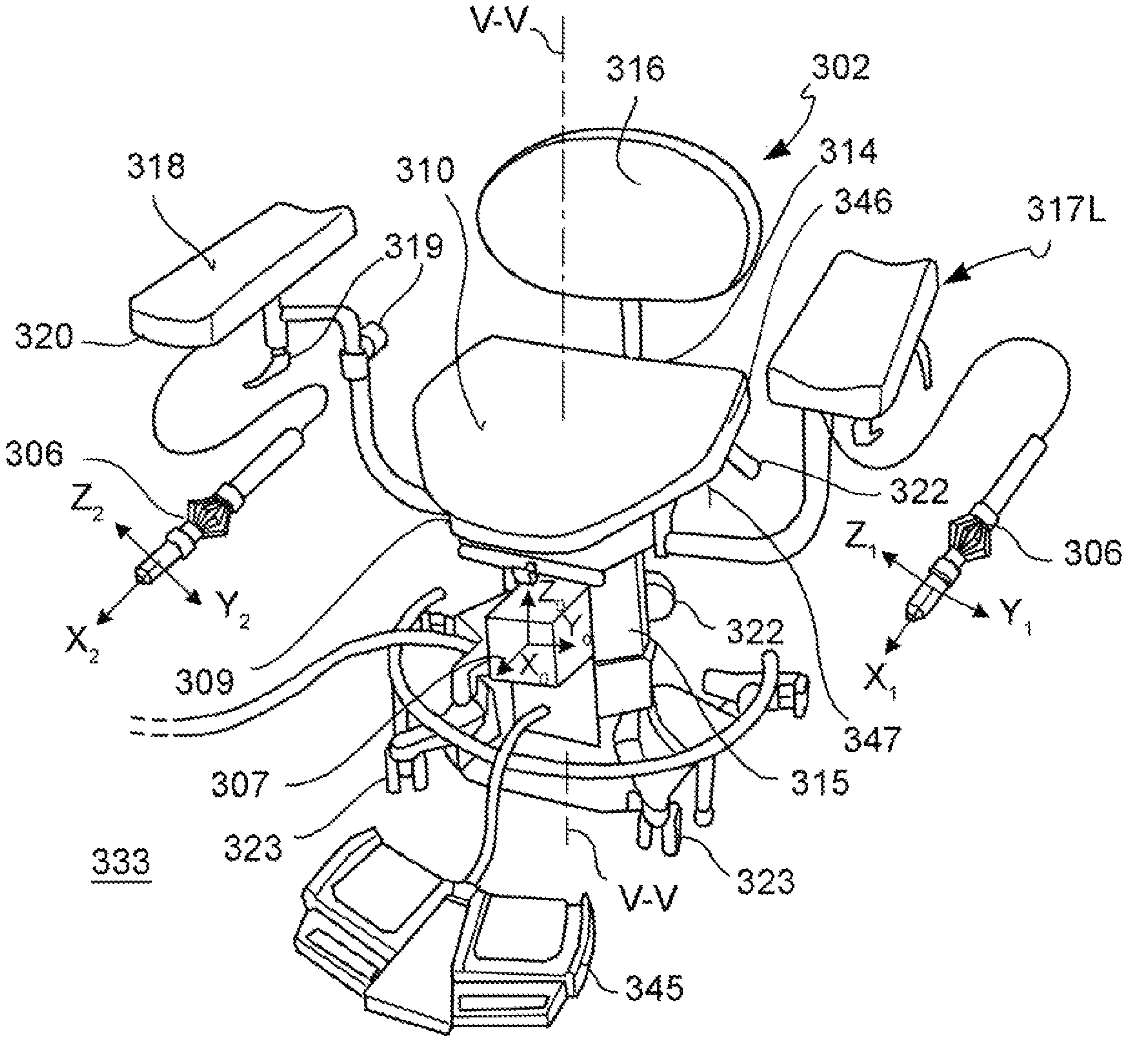
FIG. 12 is an axonometric view showing a sterile console, according to an embodiment.
Figure 13:
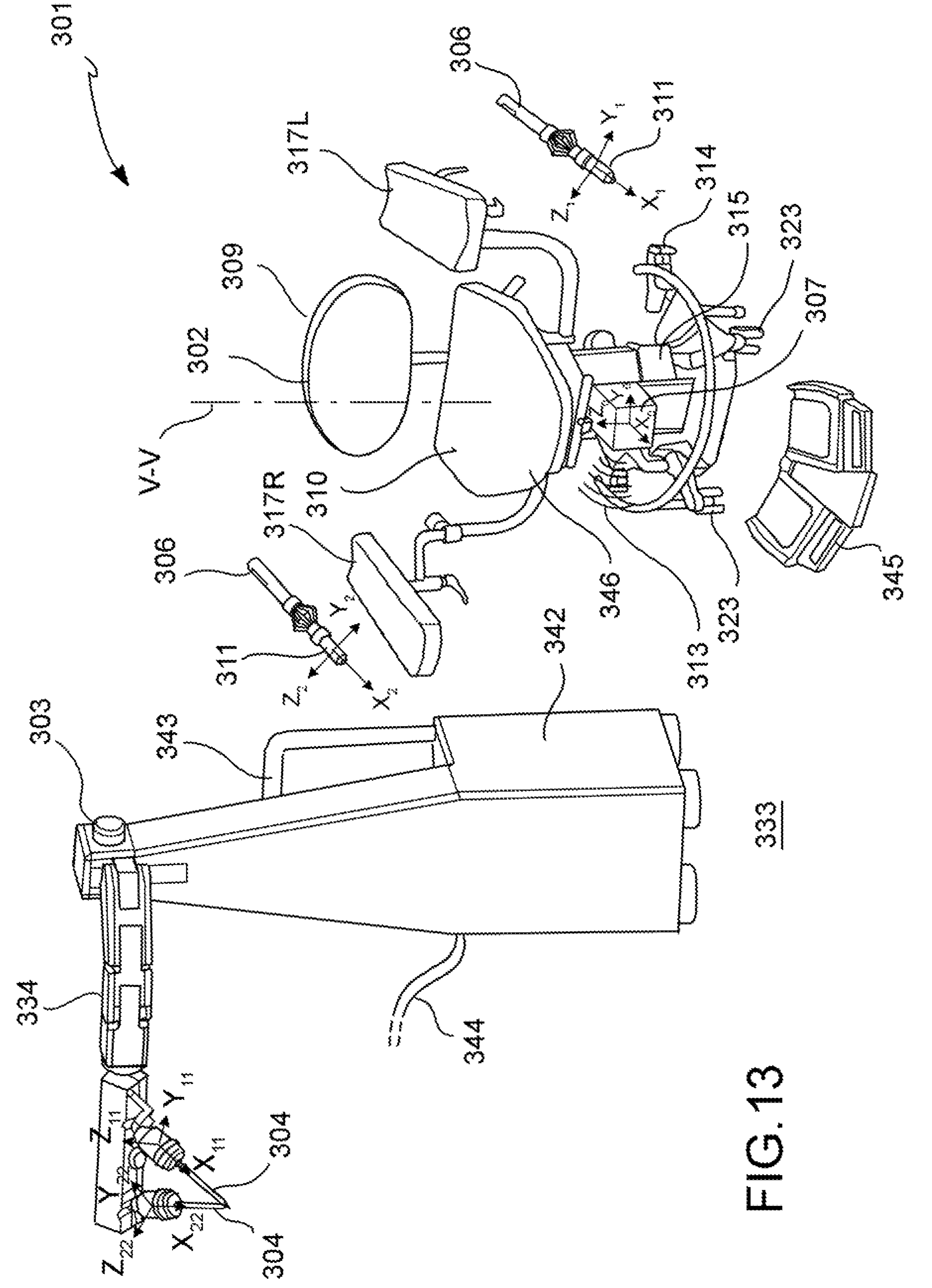
FIG. 13 is an axonometric view showing a robotic surgery system comprising a sterile console within an operating arena, according to an embodiment, wherein chair wireless connection is shown.
Figure 14:
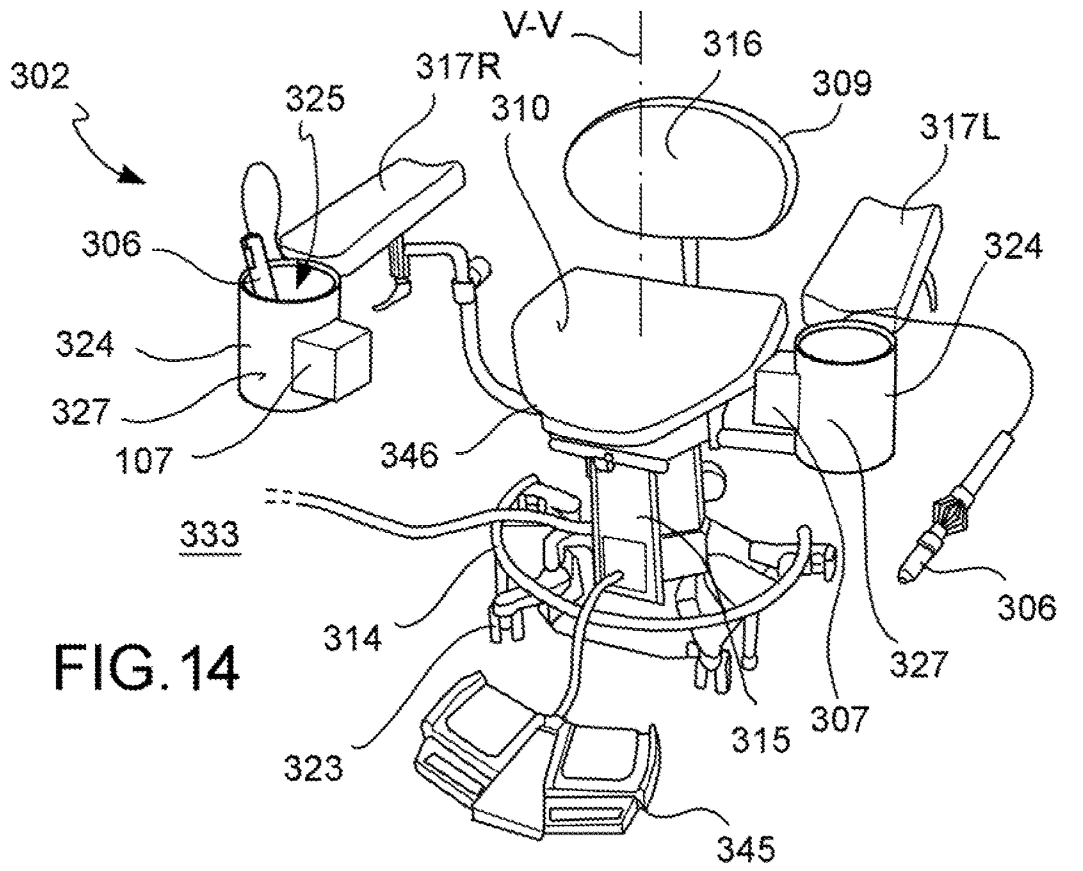
FIGS. 14 and 15 are perspective views showing a sterile console, according to an embodiment, wherein each armrest assembly associated to a field generator is shown.
Figure 15:
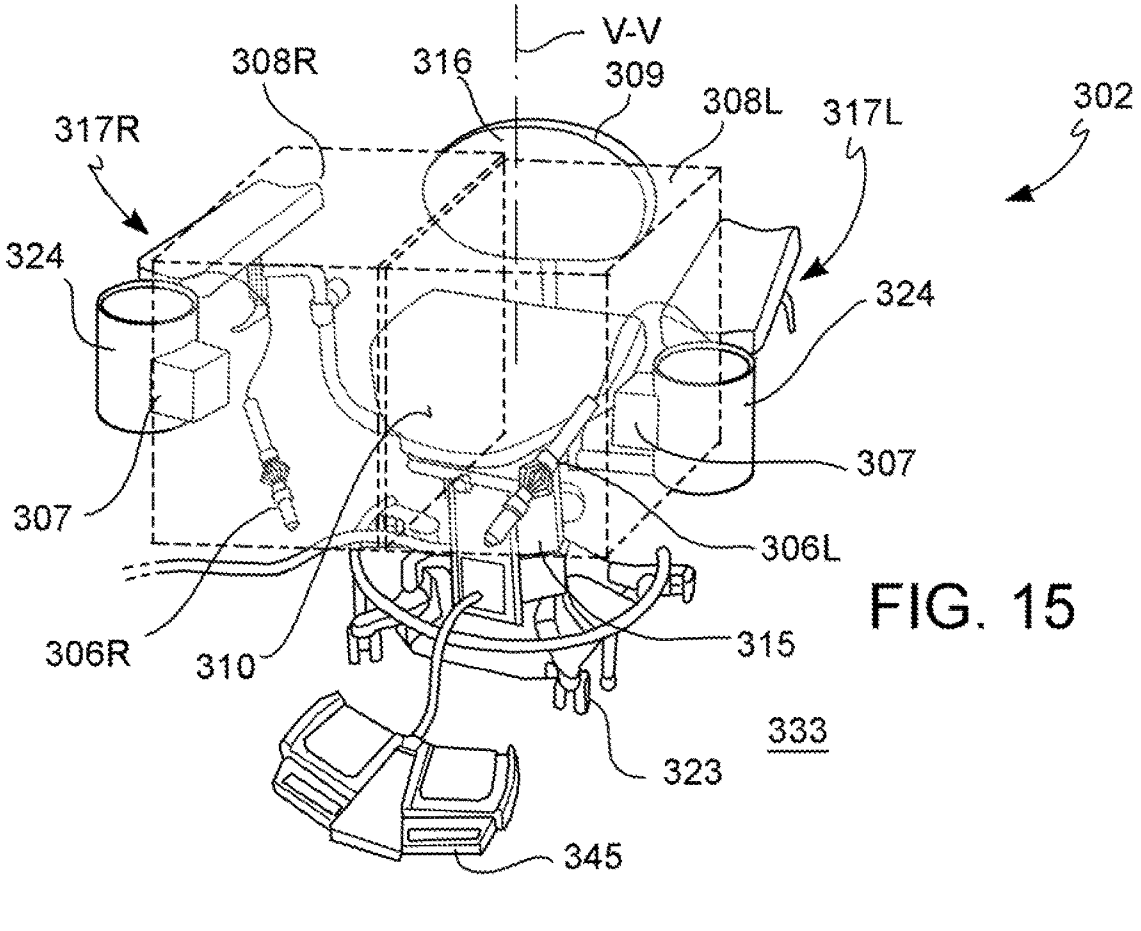
Figure 16:
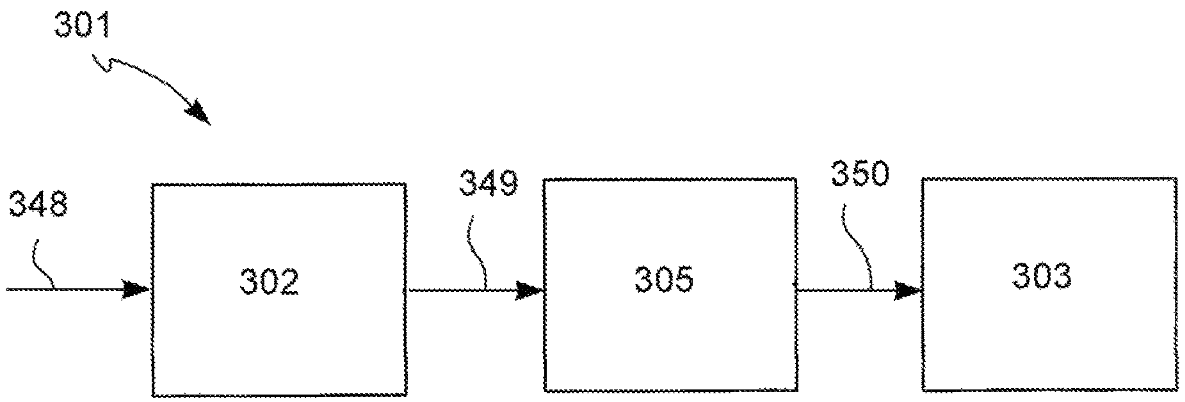
FIG. 16 is a sketch of a robotic surgery system, according to an embodiment.
Figure 17:
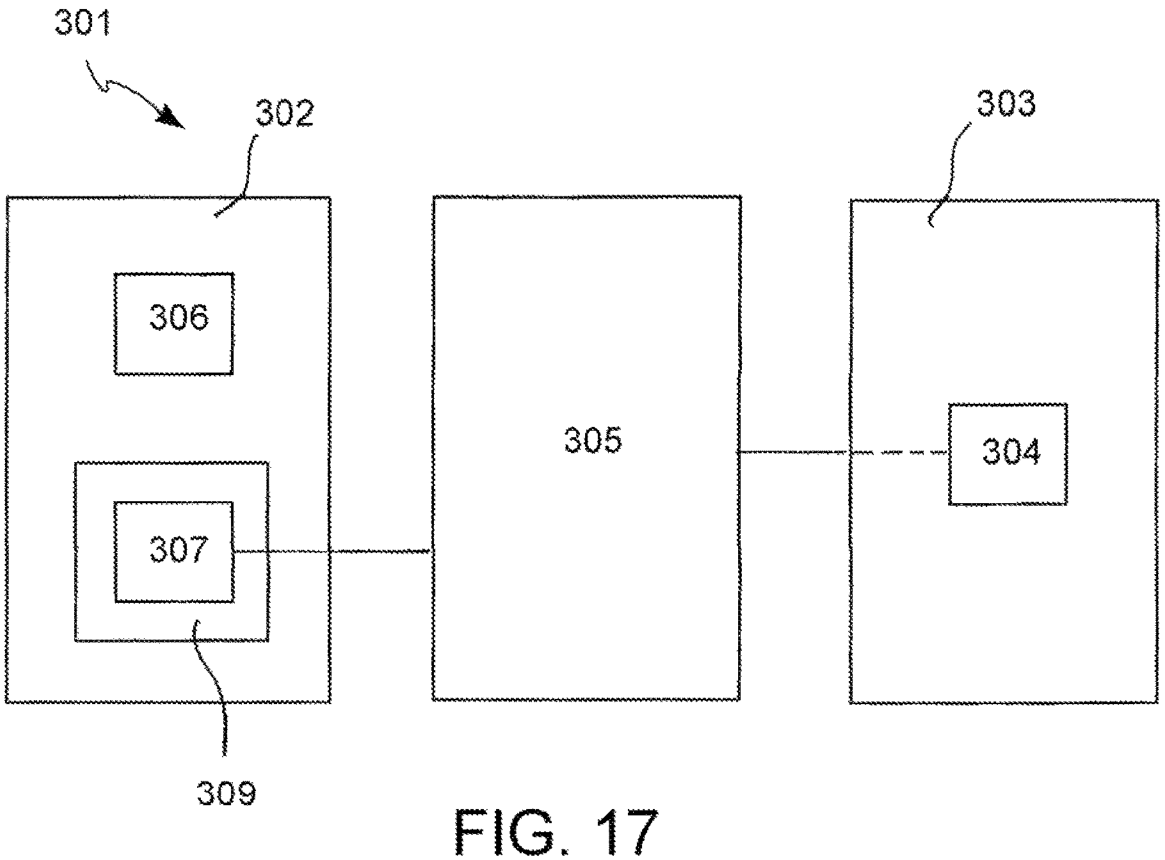
FIG. 17 is a sketch of a robotic surgery system, according to an embodiment.
Figure 18:
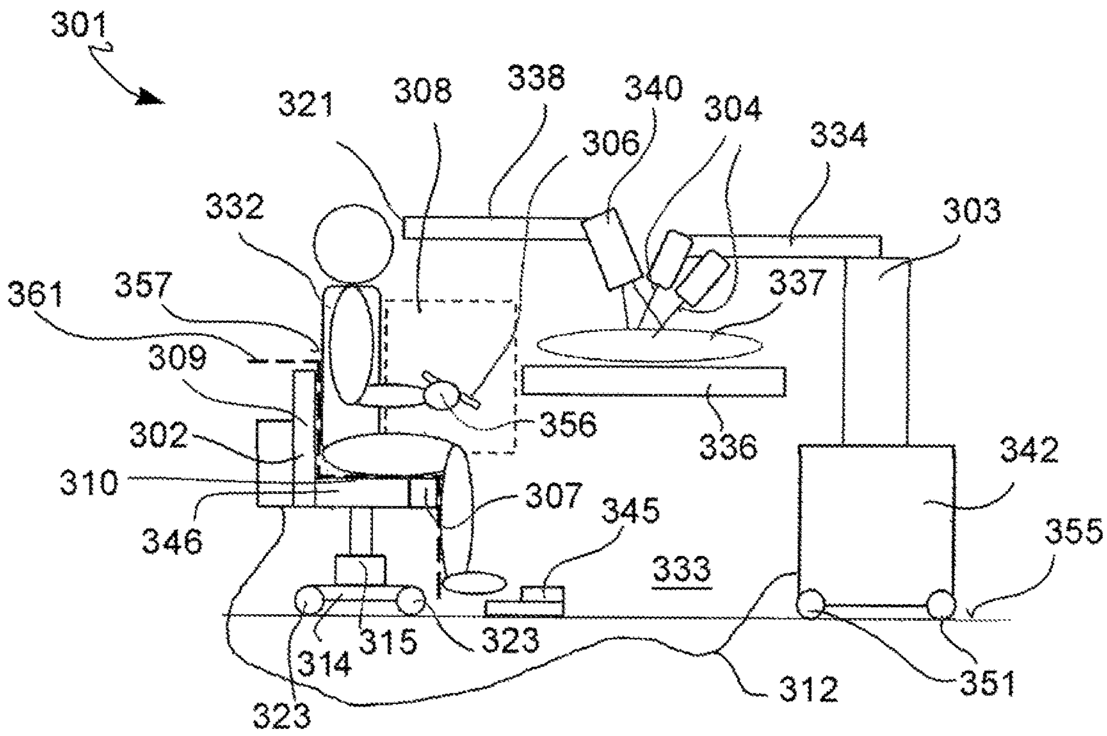
FIG. 18 is a side elevation view showing diagrammatically a sterile console according to an embodiment, within an operating arena, wherein a sterile drape is provided covering the surgical chair.
Figure 19:
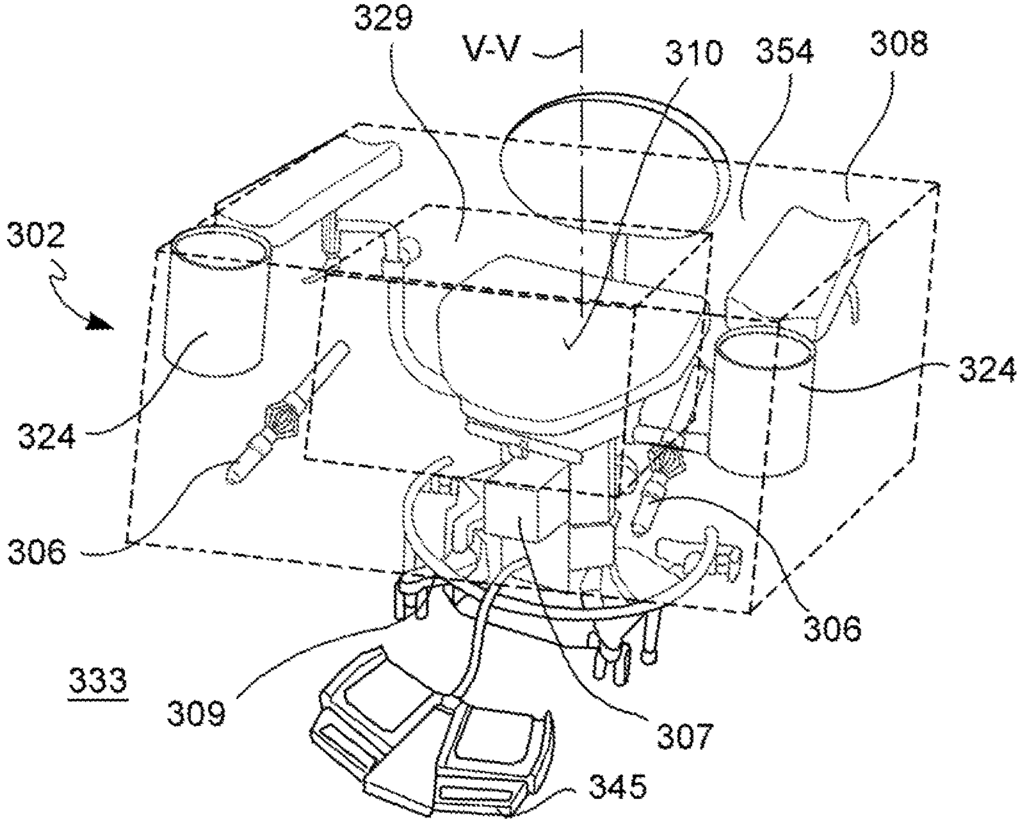
FIG. 19 is a perspective view showing a sterile console, according to an embodiment.
Figure 20:
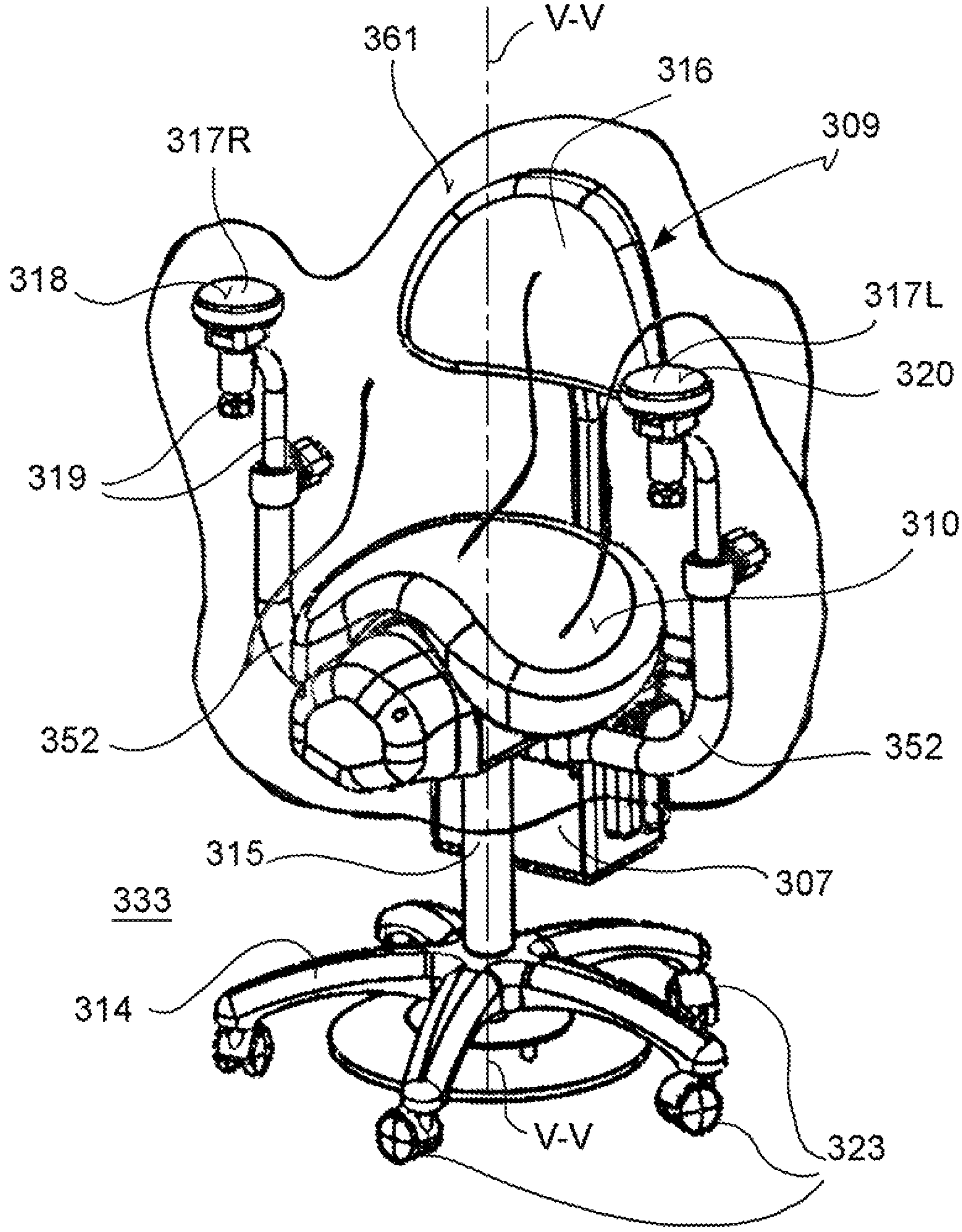
FIG. 20 is an axonometric view showing a surgical chair covered by a sterile drape, according to an embodiment.

According to a variation, as shown for example in FIG. 2, the surgeon 332 may operate from a remote location 358 and is unable to directly see the patient anatomy 337 and therefore is forced to use a remote visualization means 359, 360, such as a remote screen 359 and/or remote eyeglasses 360. Preferably, the remote location 358 is separated from the operating arena 333 by means of a wall 362 or barrier 362.

According to a preferred embodiment, the term "manipulated" referred to said master input tool 306 indicates that the master input tool can be treated or operated with or as if with hands. According to a preferred embodiment, the term "hand-held" referred to said master input tool 306 indicates that the master input tool is designed to be operated while held in a hand, for example the surgeon's hand 356. According to an embodiment, said master input tool 306 is a portable master input tool 306. According to a preferred embodiment, the term "portable" referred to said master input tool 306 indicates that the master input tool is capable to be carried or moved about.

According to an embodiment, said slave robot assembly 303 comprises at least one surgical arm 334 manipulating said surgical instrument 304. According to an embodiment, said salve robot assembly 303 comprises at least one micromanipulator 335 manipulating said surgical instrument 304. Preferably, said at least one micromanipulator 335 is directly connected in series to said surgical arm 334 forming a kinematic chain with said surgical arm 334 and manipulates said surgical instrument 304. According to an embodiment, at least two micromanipulators 335 are directly connected in series to said surgical arm 334 forming an at least two-branched kinematic chain with said surgical arm 334.

According to an embodiment, said robotic surgery system 301 comprises a control unit 305, suitable for receiving at least a position and orientation associated to said master input tool 306 and suitable for transmitting a command signal to the slave robot assembly 303 in order to actuate said surgical instrument 304.

According to a preferred embodiment, said control unit 305 is suitable for receiving a first command signal 349 containing information about said manual command 348 and to transmit a second command signal 350 containing information about said manual command 348 to the slave robot assembly 303 in order to actuate said surgical instrument 304.

According to an embodiment, said slave robot assembly 303 comprises at least one surgical arm 334 manipulating said surgical instrument 304. According to an embodiment, said salve robot assembly 303 comprises at least one micromanipulator 335 manipulating said surgical instrument 304. Preferably, said at least one micromanipulator 335 is directly connected in series to said surgical arm 334 forming a kinematic chain with said surgical arm 334 and manipulates said surgical instrument 304. According to an embodiment, at least two micromanipulators 335 are directly connected in series to said surgical arm 334 forming an at least two-branched kinematic chain with said surgical arm 334.

According to a preferred embodiment, said robotic surgery system 301, and preferably said sterile console 302 of said robotic surgery system 301, further comprises at least one tracking system comprising a field generator 307 or base component 307, suitable to detect within a predefined tracking volume 308 position and orientation of said master input tool 306.

According to a preferred embodiment, said at least one tracking system generates said predefined tracking volume 308, for example by means of a field generator, for example a magnetic field generator. According to an embodiment, said field generator 307 of the tracking system comprises a magnetic field generator and/or an optical field generator. According to a preferred embodiment, said base component 307 generates a field that defines said predefined tracking volume 308.

Said master input tool 306 defines a first frame of reference X1,Y1,Z1; X2,Y2,Z2 attached thereto. In other words, said robotic surgery system 301 comprises a first frame of reference X1,Y1,Z1; X2,Y2,Z2 attached to said master input tool 306.

Said sterile console 302 comprises at least one surgical chair 309 comprising at least one seating surface 310 for the surgeon to seat thereon during surgery. According to an embodiment, said surgical chair 309 is a stool. Preferably, said sterile console 302 comprises said surgical chair 309 and said at least one master input tool 306.

Said field generator 307 of the tracking system defining a second frame of reference X0,Y0,Z0 attached thereto. In other words, said robotic surgery system 301 comprises a second frame of reference X0,Y0,Z0 attached to said field generator 307 of the tracking system.

Said field generator 307 of the tracking system is designed to detect within said predefined tracking volume 308 position and orientation of said master input tool 306.

Preferably, said predefined tracking volume 308 is fixed in space with respect to said field generator 307. In other words, said tracking volume 308 is integral with said field generator 307 of the tracking system.

Advantageously, said position and orientation of the master input tool 306 detected by said field generator 307 of the tracking system is a position and orientation of said first frame of reference X1,Y1,Z1; X2,Y2,Z2 with respect to said second frame of reference X0,Y0,Z0 within said tracking volume 308.

According to an embodiment, said robotic surgery system 301 comprises a control unit 305, suitable for receiving at least a position and orientation associated to said master input tool 306 and suitable for transmitting a command signal to the slave robot assembly 303 in order to actuate said surgical instrument 304.

According to a preferred embodiment, said control unit 305 is suitable for receiving a first command signal 349 containing information about said manual command 348 and to transmit a second command signal 350 containing information about said manual command 348 to the slave robot assembly 303 in order to actuate said surgical instrument 304.

According to an embodiment, said slave robot assembly 303 comprises at least one surgical arm 334 manipulating said surgical instrument 304. According to an embodiment, said salve robot assembly 303 comprises at least one micromanipulator 335 manipulating said surgical instrument 304. Preferably, said at least one micromanipulator 335 is directly connected in series to said surgical arm 334 forming a kinematic chain with said surgical arm 334 and manipulates said surgical instrument 304. According to an embodiment, at least two micromanipulators 335 are directly connected in series to said surgical arm 334 forming an at least two-branched kinematic chain with said surgical arm 334.

Advantageously, said field generator 307 of the tracking system is integral with a portion of the surgical chair 309 so that, when the surgeon seats onto said seating surface 310 of the surgical chair 309 and hand-holds said at least one master input tool 306, said master input tool 306 is located within said tracking volume 308 and the position and orientation thereof can be detected by the tracking system. Moreover, in this way, the tracking volume 308 can be moved and/or relocated along with said portion of the surgical chair 309 integral thereto.

According to a preferred embodiment, said field generator 307 of the tracking system is integral to said seating surface 310 of the surgical chair 309.

According to a preferred embodiment, said surgical chair 309 comprises at least one seating detector 328 detecting when the surgeon 332 is seated on said surgical chair 309. For example, said seating detector 328 comprises at least one load cell located onto, or within, or underneath said seating surface 310. Preferably, said seating detector 328 is operatively connected to said control unit 305.

According to a preferred embodiment, said master input tool 306 is designed to be hand-held by the surgeon 332 within said tracking volume 308 when said surgeon 332 seats onto said seating surface of said surgical chair 309. Preferably, said master input tool 306 is designed to be hand-held by the surgeon 332 within said tracking volume 308 exclusively when said surgeon 332 seats onto said seating surface of said surgical chair 309.

According to a preferred embodiment, said robotic surgery system 301 comprises at least one master input tool supporting element 324, or tool supporting element 324, providing a support for the master input tool 324, preferably for the master input tool 306 to rest thereon, when the surgeon does not hand-hold said at least one master input tool 306.

According to a preferred embodiment, said tool supporting element 324 is integral with a portion of said surgical chair 309 so that when the surgeon 332 seats onto said seating surface 310 of the surgical chair 309 the surgeon 332 itself can manually laid down said at least one master input tool 306 onto said tool supporting element 324.

Thanks to the provision of such a tool supporting element 324 integral with a portion of said surgical chair 309, the position and orientation of said master input tool 306 detected by the tracking system, when said tool supporting element 324 supports said master input tool 306, can remain unchanged also if the surgical chair 309 is moved in respect of said slave robot assembly 303.

Preferably, said master input tool 306 is suitable to be laid down on said tool supporting element 324 by said surgeon 332 when seats onto said surgical chair 309. In other words, during surgery, said master input tool 306 can be manually laid down onto said tool supporting element 324 by the surgeon 332.

According to a preferred embodiment, a predefined tracking sub-volume 329 is defined within said tracking volume 308. In other words, said tracking volume 308 comprises at least one tracking sub-volume 329. Preferably, said tracking sub-volume is contained in its entirety within said tracking volume 308. Preferably, said field generator 307 of the tracking system generates said tracking sub-volume 329 Preferably, said control unit 305 defines the extent of said tracking sub-volume 329.

According to an embodiment, if the master input tool 306 is detected as being located within said tracking sub-volume 329, then the control unit 305 sends command signal to actuate said slave surgical instrument 304, and wherein if the master input tool 306 is detected as being located within said tracking volume 308 but outside said tracking sub-volume 329 (e.g., within said safety tracking volume portion 354), then the control unit 305 disables the paired actuation of said surgical instrument 304.

Thanks to said tracking sub-volume 329, an operation workspace can be defined, wherein the master input tool 306 when is detected as being located within said sub-tracking volume 329 transmits through said control unit 305 command signal to said slave robot 303 in order to actuate the paired slave surgical instrument 304. At the same time, the provision of said tracking sub-volume defines by contrast within said tracking volume 308 at least one safety tracking volume portion 354, wherein if the master input tool 306 is detected as being located within said safety tracking volume, then the control unit 305 is prevented from sending command signal to actuate said surgical instrument 304. The provision of such a safety tracking volume portion 354 improves the safety of the patient during surgery, as is reduced to minimum the risk of transmission of unwanted command potentially able for actuating said surgical instrument 304 dangerously in an uncontrolled manner.

According to an embodiment, said at least one master input tool 306 comprises at least one sensing device 311 detecting at least the position, preferably at least the position and the orientation, of said master input tool 306 within said predefined tracking volume 308. Preferably, said sensing device 311 is integral with said master input tool 306.

According to an embodiment, said sensing device 311 being operatively connected to said field generator 307. Preferably, said sensing device 311 being operatively connected to said field generator 307 by means of electromagnetic communication. According to an embodiment, said sensing device 311 comprises at least one sensor integral with at least a portion of the master input tool 306 and at least a wired connection to said field generator 307. According to an embodiment, said sensing device 311 comprises at least one sensor integral with at least a portion of the master input tool 302 and at least a wireless connection to said field generator 307.

According to a preferred embodiment, said surgical chair 309 is mechanically unconstrained from the slave robot assembly 303, so as to prevent the propagation by mechanical contact of vibrational motion from the surgical chair 309 to the slave robot assembly 303. In this way, is reduced the risk of unwanted commands transmittal to the slave surgical robot 303, and particularly to said slave surgical instrument 304.

According to an embodiment, said sterile console 302 comprising said surgical chair 309 is operatively connected to said slave robot assembly 303, preferably by means of electromagnetic communication. According to an embodiment, said sterile console 302 comprising said surgical chair 309 is operatively connected to said slave robot assembly 303 by means of a chair wired connection 312. According to an embodiment, said sterile console 302 comprising said surgical chair 309 is operatively connected to said slave robot assembly 303 by means of a chair wireless connection 313. According to an embodiment, said chair wired connection 312 and/or said chair wireless connection 313 provides power supply to said sterile console 302.

According to an embodiment, said field generator 307 defines said second frame of reference X0,Y0,Z0 integral with said field generator 307, and wherein said at least one sensing device 311, detecting first frame of reference X1,Y1,Z1; X2,Y2,Z2, determines at least the position of said sensing device 311 within said tracking volume 308. In this way, sensing device 311 determines at least the position of said master tool assembly 306 integral with said sensing device 311 within said predefined tracking volume 308.

According to a preferred embodiment, a sterile console 302 is defined, wherein said sterile console 302 comprises at least said at least one master input tool 306, said at least one surgical chair 309 and said at least one tool supporting element 324, and wherein said sterile console 302 cooperates with said slave robot assembly 303 for controlling said surgical instrument 304.

According to an embodiment, the sterile console 302 comprises at least a pair of master input tools 306.

Preferably, each master input tool 306 comprises, preferably integral thereto, at least one sensing device 311, wherein said sensing devices 311 cooperate to detect at least the mutual position of said pair of master input tool 306.

According to an embodiment, said sensing device 311 comprises at least one sensor detecting the local magnetic field generated by said field generator 308.

According to an embodiment, said sterile console 302 comprising said surgical chair 309 is located within said operating arena 333. In this way, communication among surgical team members is enhanced. According to an embodiment, said operating arena 333 is all contained in a single operating room.

Therefore, in said robotic surgery system 301, said surgical chair 309 is not located outside the operating arena 333 such as in a remote location 358.

According to a preferred embodiment, said robotic surgery system 301 further comprises a patient supporting structure 336, for example an operating table 336 or the like, forming a support for the patient anatomy 337 to rest thereon during surgery and located within the operating arena 333.

According to a preferred embodiment, said robotic surgery system 301 further comprises a surgery vision assembly 338 showing the surgery to the surgeon 332. According to an embodiment, said surgery vision assembly 338 comprises at least one image acquisition device 340, suitable for acquiring real-time images of the on-going surgery, and at least one image showing device, for example a display 321 and/or a microscope ocular device 339.

According to an embodiment, said surgery vision assembly 338 comprises at least a 3D-eyeglasses cooperating with a display 321, preferably a 3D-display, for showing the surgery to the surgeon 332 placed at said sterile console 302 within the operating arena 333.

Thanks to the provision of such a surgery vision assembly 338 and said sterile console 302 located within the operating arena 333, the surgeon may alternate hand surgery with robotic surgery in the same intervention.

According to an embodiment, said robotic surgery system 301 comprises at least one robot cart 342 comprising at least one cart ground contact unit 351 and a cart handle 343, said cart handle 343 being suitable for moving at least a portion of the robotic surgery system 301, preferably said slave robot assembly 303, at least within the operating arena 333. Preferably, said robot cart 342 forms a mechanical and structural support, preferably a movable mechanical and structural support, for the slave robot assembly 303.

According to an embodiment, said robot cart 342 is connected to a power supply cable 344.

According to an embodiment, said robot cart 342 comprises said control unit 305.

According to an embodiment, said surgical chair 309 comprises said control unit 305. Preferably, said control unit 305 is integral with said field generator 307.

According to an embodiment, said surgical chair 309 comprises a chair base structure 314 providing structural support to a seating lower portion 315. In this way, the chair base structure 314 provides, through said seating lower portion 315, structural support to said seating surface 310. Preferably, said chair base structure 314 comprises ground contact units 323 such as wheels.

According to an embodiment, said chair base structure 314 comprises said field generator 307 so that said tracking volume 308 is integral with said chair base structure 314.

According to an embodiment, said surgical chair 309 comprises a seating lower support portion 315 integral with said seating surface 310. Preferably, said seating lower support portion 315 is located under said seating surface 310.

According to an embodiment, said surgical chair 309 comprises a seating element body 346. According to an embodiment, said seating element body 346 comprises said seating surface 310. According to an embodiment, said seating element body 346 comprises a lower seating body portion 347 facing the ground 355. Preferably, said seating element body 346 is integral with said lower seating support portion 315.

According to an embodiment, said seating lower support portion 315 comprises said field generator 307 so that said tracking volume 308 is integral with said seating surface 310.

According to an embodiment, said seating lower support portion 315 is telescopically connected to said chair base structure 314. In this way, the height from soil of the seating surface 310 of said seating lower support portion 315 is telescopically adjustable.

According to an embodiment, said surgical chair 309 comprises a seatback portion 316. In this way, the surgeon can lean back against said seatback portion during surgery.

According to an embodiment, said surgical chair 309 comprises a seat adjustment device 322 providing the surgical chair 309, and preferably said seating lower support portion 315 of the surgical chair 309, with the capability of rolling around a substantially vertical roll axis V-V.

According to a preferred embodiment, said seating lower support portion 315 may pivot around a vertical axis V-V with respect of said seat base structure 314. Preferably, the filed generator 307 is integral with said seating lower support portion 315. Thereby, the tracking volume 308 is integral with the seating surface of the surgical chair 309 of the sterile console 302 during the rolling around the substantially vertical roll axis V-V. In this way, it is allowed for the surgeon while seated on the surgical chair 309 to pivot during surgery, without loosing control over the surgical instrument 306, that is to say without for this reason transmit unwanted commands to the slave surgical instrument 306.

According to an embodiment, said seat adjustment device 322 provides the capability of adjust the height form soil of the seating surface 310.

According to a preferred embodiment, said surgical chair 309 is movable, preferably movable at least within said operating arena 333, in at least one direction co-planar with the seating surface 310. According to a preferred embodiment, said seating surface 310 of the surgical chair 309 can pivot about a vertical axis V-V. According to a preferred embodiment, said seating surface 310 of the surgical chair 309 can be adjusted in height.

According to a preferred embodiment, said seating surface 310 of the surgical chair 309 can be rotated about a vertical axis V-V.

According to a preferred embodiment, said seating surface 310 of the surgical chair 309 can be adjusted in height in respect of the floor, for example the floor of the operating arena 333.

Thanks to the provision of said field generator 307 of the tracking system integral with said surgical chair 309, the detection of position and orientation of the master input tool 306 is achieved regardless of the position of the seating surface 310 within the operating arena 333. In other words, as the tracking volume 308 and the tracking sub-volume 329 are integral with said field generator 307 associated to said surgical chair 309, the detection of the first frame of reference X1,Y1,Z1; X2,Y2,Z2 is unrelated to the position of the surgical chair 309 within the operating arena 333. That allows the surgeon 332 the faculty to choose, either real-time choice or planned choice, the best place for locating the surgical chair 309 for seating thereto during surgery.

According to an embodiment, said surgical chair 309 comprises at least one ground contacting wheel 323. The provision of said at least one ground contacting wheel 323 allows to move the surgical chair 309 and thus the field generator 307 and the predetermined filed volume 308 integral thereto at least within the operating arena 333. Preferably, said ground contacting wheel are connected to said chair base structure 314.

According to a preferred embodiment, said surgical chair 309 comprises at least one armrest assembly 317L; 317R comprising an armrest surface 318, designed to form a resting surface for at least a portion of a surgeon's forearm.

According to a preferred embodiment, said at least one of said armrest assemblies 317L; 317R has a rounded shape, so that to allow the surgeon to rest only the elbow providing enhanced range of movement for the surgeon's forearms. In other words, said armrest surface 318 is substantially round. Preferably, the armrest has a substantially cylindrical volume. Preferably, said armrest surface 318 forms a bulge.

Preferably, said surgical chair 309 comprises a pair of opposite armrest assemblies 317L, 317R, located opposite to one another in respect of said seating surface 310. In this way, the surgical chair 309 comprises a first armrest assembly 317L, or left armrest assembly 317L, and a second armrest assembly 317R, or right armrest assembly 317R.

According to an embodiment, at least one of said armrest assemblies 317L; 317R comprises said field generator 307 of the tracking system so that the second frame of reference X0,Y0,Z0 is integral with at least a portion of said at least one armrest assemblies 317L; 317R.

According to an embodiment, at least one of said armrest assemblies 317L; 317R comprises a display 321 showing a portion of an user interface or touch screen. According to an embodiment, said at least one display 321 showing a portion of the slave surgical instrument 304 during surgery.

According to an embodiment, at least one of said armrest assemblies 317L; 317R comprises said at least one tool supporting element 324 providing a support for the master input tool 306, preferably a support for the master input tool 306 to rest thereon, wherein said tool supporting element 324 is connected integral to said armrest element 320.

According to an embodiment, said armrest assembly 317L; 317R is connected to said seating lower support portion 315 by means of at least one connecting structure 352, for example a tubular connecting element. In this way, at least a portion of the armrest assembly 317L; 317R can be integral with the seating surface 310.

According to an embodiment, said armrest assembly 317L; 317R comprises at least one armrest element 320 having an armrest body comprising said at least one armrest surface 318.

According to an embodiment, said at least one armrest assembly 317L; 317R comprises an armrest adjustment device 319, suitable to adjust at least the height of the armrest surface 318 in respect of the height of said seating surface 310.

According to an embodiment, said armrest adjustment device 319 comprises a telescopically extending portion 353, telescopically movable in respect of said seating lower support portion 315. Preferably, said telescopically extending portion 353 is telescopically extendable in respect of said connecting structure 352.

According to an embodiment, said armrest adjustment device 319 comprises at least a spherical joint connected to said armrest element 320, so as to be suitable for adjust the spatial orientation of said armrest element 320.

Thanks to said armrest adjustment device 319, it is allowed to select a suitably height from the seating surface 310 of said armrest surface 318, as well as suitably move the pitch and/or yaw and/or roll degree-of-freedom of said armrest element 320.

According to an embodiment, each of said pair of armrest assemblies 317L; 317R comprises one field generator 307. In this way, two predetermined tracking volumes 308L, 308R are defined, wherein a first predefined tracking volume 308L is integral with at least a portion of said left armrest assembly 317L and a second tracking volume 308R is integral with at least a portion of said right armrest assembly 317R. According to an embodiment, said two predetermined tracking volumes 308L, 308R are connected together. Preferably, a left master input tool 306L position and orientation is detected within said first tracking volume 3008L and a right master input tool 306R position and orientation is detected within said second tracking volume 308R.

According to an embodiment, each of said armrest assemblies 317L; 317R of said pair of armrest assemblies comprises said armrest adjustment device 319, so that each of said armrest assemblies 317L; 317R is adjustable independently from the other. In this way, the surgeon 332 can adjust the height from seating surface 310 of said armrest surface 318 of said left armrest assembly 317L independently from the right armrest assembly 317R, and vice versa.

According to an embodiment, said armrest assembly 317L; 317R comprises said tool supporting element 324 providing a support for the master input tool 306 to rest thereon. The provision of said tool supporting element 324 makes the sterile console 302 suitable to safely comprise a master input tool 306 mechanically unconstrained from both said surgical chair 309 and said slave robot assembly 303, as well as from said robot cart 342 and other portions of said robotic surgery system 301. Moreover, in this way the surgeon's comfort is greatly enhanced, as the surgeon 332 can drop the master input tool 306 while not in use, avoiding to holding the master input tool in hand while not in use.

According to an embodiment, said tool supporting element 324 comprises a cup-shaped body defining a tool receptacle 325. According to an embodiment, said tool supporting element 324 comprises a cup bottom wall 326 and at least one cup lateral wall 327. According to an embodiment, said tool supporting element 324 is connected integral to said armrest element 320.

According to an embodiment, said tool supporting element 324 comprises a hook-shaped body for the master input tool to be hung thereto.

According to a preferred embodiment, said surgical chair 309 comprises at least one seating detector 328 detecting when the surgeon is seated on said surgical chair 309.

Preferably, said seating detector 328 cooperates with said control unit 305 for transmitting a predefined command signal to said slave robot assembly 303 in order to actuate said surgical instrument 304 when the surgeon is seated on said surgical chair 309 and/or in order to avoid to actuate said surgical instrument 304 when the surgeon 332 is not seated on said surgical chair 309.

According to a preferred embodiment, said surgical chair 309 further comprises at least one locking device suitable to selectively block at least one degree of freedom of motion of said surgical chair 309, said at least one locking device cooperating with said at least one seating detector 328 to block said at least one degree of freedom of motion of said surgical chair 309 when said seating detector 328 detects the surgeon as being seated on said surgical chair 309, preferably on said seating surface 310. Preferably, said locking device provides a mechanical action of locking said at least one degree of freedom of motion of said surgical chair 309 within the operating arena 333.

According to an embodiment, said locking device selectively blocks at least the degree of freedom of motion provided by said at least one ground contacting wheel 323. In this way, when the surgeon 332 seats, i.e. during surgery, on said surgical chair 309, the latter cannot be relocated within the operating arena 333, improving the safety of the whole surgical team during surgery.

According to an embodiment, said locking device selectively blocks at least the degree of freedom of motion provided by said seat adjustment device 322. In other words, said locking device blocks the roll around a vertical axis V-V degree-of-freedom and/or the height from soil of said seating surface 310. In this way, the surgical chair 309 cannot be adjusted when the surgeon seats, i.e. during surgery, on said surgical chair.

According to an embodiment, said locking device selectively blocks at least the degree of freedom of motion provided by said armrest adjustment device 319. This feature is particularly advantageous when provided in combination with the embodiment wherein each of said pair of armrest assemblies 317L; 317R comprises one field generator 307.

According to an embodiment, said seating detector 328 comprises at least one load cell. In this way the load cell senses the surgeon's load on at least a portion of said surgical chair 309.

According to an embodiment, said seating detector 328 is associated to said seating surface 310, for detecting the surgeon's load carried onto said seating surface 310. In other words, said seating surface 310 comprises said seating detector 328.

According to an embodiment, said seating detector 328 is associated to said seating element body 346, for detecting the surgeon's load carried onto said seating element body 346. In other words, said seating element body 346 comprises said seating detector 328.

According to an embodiment, said seating detector 328 is associated to said seating lower support portion 315, for detecting the surgeon's load carried onto said seating lower support portion 315. In other words, said seating lower support portion 315 comprises said seating detector 328.

According to an embodiment, said seating detector 328 is associated to said seatback portion 316, for detecting the surgeon's contact onto said seatback portion 316. In this way, said seating detector 328 detects when the surgeon's back 357 rest on said seatback portion 316.

According to an embodiment, said seating detector 328 is associated to said armrest surface 318, for detecting the surgeon's contact onto said seatback portion 316. In other words, said armrest surface 318 comprises said seating detector 328.

According to an embodiment, said seating detector 328 is associated to said armrest surface 318 of both said pair of armrest assemblies 317L, 317R. In other words, said armrest surface 318 of each armrest assembly 317L; 317R of said pair of armrest assemblies 317L, 317R comprises said seating detector 328.

According to an embodiment, said seating detector 328 comprises a plurality of seating detector sensing elements, for examples load cells.

According to an embodiment, said field generator 307 is detachably connected to the surgical chair 309, in such way that the surgical chair devoid of said field generator 307 can be sterilized. That allows the use of said surgical chair within sterile environment, for example the operatory room.

According to an embodiment, said sterile console 302 comprises a clutch device 345 that, when in activated condition, prevents the slave robot assembly 303 to receive any command signal containing a manual command detected by said sterile console 302. In this way, the clutch device 345 prevents unintended motion transmittal to the slave surgical instrument 304.

According to an embodiment, said clutch device 345 is operatively connected to said surgical chair 309, preferably to said field generator 307, by means of a wired or wireless connection.

According to an embodiment, said master input tool 306 is mechanically unconstrained from both said surgical chair 309 and said slave robot assembly 303, in such way that said master input tool 306 being naturally movable, rotatable and spinnable, preferably multiple times, by the surgeon within said predefined tracking volume 308.

According to an embodiment, said master input tool 306 is operatively connected to said field generator 307 by means of a tool wired connection 330.

According to an embodiment, said master input tool 306 is operatively connected to said field generator 307 by means of a tool wireless connection 331.

According to an embodiment, said surgical chair 309 is operatively connected to said slave robot assembly 303 by means of a chair wired connection 312.

According to an embodiment, said surgical chair 309 is operatively connected to said slave robot assembly 303 by means of a chair wireless connection 313.

According to an embodiment, said control unit 305 is located in its entirety within said seat body 314.

According to an embodiment, said control unit is located in its entirety within said seating lower support portion 315.

Said robotic surgery system 301 associable with said sterile console 302 comprises at least one slave robot assembly 303 comprising at least one surgical instrument 304, designed to operate on a patient anatomy, and a control unit 305.

Said sterile console 303 for a robotic surgery system 301 comprises:

- at least one master input tool 306 mechanically ungrounded and suitable to be hand-held by a surgeon during surgery;
- at least one surgical chair 309 comprising at least one seating surface 310 for the surgeon 332 to seat thereon during surgery;
- at least one tracking system, suitable to detect position and orientation of said at least one master input tool 306 within a predefined tracking volume 308;
- at least one tool resting element 324 providing a support for said at least one master input tool 306 to rest thereon when the surgeon does not hand-hold said at least one master input tool 306.

According to a preferred embodiment, said at least one master input tool 306 defines at least one first frame of reference X1,Y1,Z1; Y2,Y2,Z2 attached thereto;

According to a preferred embodiment, said tracking system comprises a field generator 307 defining a second frame of reference X0,Y0,Z0 attached thereto.

According to a preferred embodiment, said tracking volume 308 is integral with said field generator 307 of the tracking system.

Advantageously, the position and orientation detected by said tracking system is the position and orientation of said at least one first frame of reference X1,Y1,Z1; X2,Y2,Z2 with respect of the second frame of reference X0,Y0,Z0, so that said control unit 305 of the robotic surgery assembly 301 is suitable for receiving information about said position and orientation of said at least one master input tool 306 within said tracking volume 308 and is suitable for transmitting a command signal to the slave robot assembly 303 in order to actuate said at least one surgical instrument 304.

Advantageously, said field generator 307 of the tracking system is integral with a portion of the surgical chair 309 so that, when the surgeon seats onto said seating surface 310 of the surgical chair 309 and hand-holds said at least one master input tool 306, said master input tool 306 is located within said tracking volume 308 and the position and orientation thereof can be detected by the tracking system.

According to a preferred embodiment, said tool resting element 324 is integral with a portion of said surgical chair

309 so that when the surgeon seats onto said seating surface 310 of the surgical chair 309 the surgeon itself can manually laid down said at least one master input tool 306 onto said tool resting element 324.

According to a preferred embodiment, the position and orientation of said master input tool 306 detected by the tracking system, when said tool resting element 324 supports said master input tool 306, can remain unchanged also if the surgical chair 309 is moved in respect of said slave robot assembly 303.

According to an embodiment, said surgical chair 309 comprises said control unit 305.

According to a preferred embodiment, said sterile console 302 is defined according to any one of the embodiments described above.

According to a general embodiment, it is provided an operating arena 333 comprising a sterile console 302 according to any of the embodiments described above.

Said operating arena 333 further comprises at least one slave robot assembly 303 comprising at least one surgical instrument 304 designed to operate on a patient anatomy 337 and preferably also a patient supporting structure 336 forming a support for a patient anatomy 337 to rest thereon during surgery and located within the operating arena 333. Preferably, said patient supporting structure 336 comprises an operatory bed or the like.

According to an embodiment, said operating arena 333 comprises a robotic surgery assembly 301 according to any one of the embodiments described above.

According to an embodiment, said operating arena 333 comprises a surgery vision assembly 338 showing the surgery to the surgeon 332. Preferably, said surgery vision assembly 338 comprises at least one image acquisition device 340, suitable for acquiring real-time images of the on-going surgery, and at least one image showing device, for example a display 321 and/or a microscope ocular device 339.

According to a preferred embodiment, said operating arena 333 comprises a sterile volume and said sterile console 302 is located within the sterile volume of the operating arena 333 and protected by means of covering of a sterile drape 361.

It follows a description of a method to perform surgery.

According to a general embodiment, a method to perform surgery comprises the following steps:

seating on said surgical chair 309;

hand-holding said master input tool 306;

bringing said master input tool within a predefined tracking volume 308;

sending said command to a control unit 305 to activate a slave robot 303;

According to a preferred mode of operation, said method comprises the following further step of controlling the motion of said slave robot 303 by handling said master input tool 306.

According to a preferred embodiment, said method comprises the following further step of providing a robotic surgery system 301 according to any one of the embodiments previously described.

According to a preferred mode of operation, said method comprises the following further step of activating said seating detector 328. Preferably, this step of activating is carried out before the step of sending said command to a control unit 305 to activate a slave robot 303.

According to a preferred mode of operation, the step of seating is carried out preferably by seating onto said seating surface 310 of the surgical chair 309.

According to a preferred mode of operation, the step of hand-holding comprises the sub-step of getting hold in hand said master input tool 306 from said tool supporting element 324.

According to a preferred mode of operation, the step of bringing is carried out by moving said master input tool 306 from said tool supporting element 324, which is preferably located within said safety tracking volume portion 354, to said sub-tracking volume 329.

According to a preferred mode of operation, the step of sending a command, preferably is carried out by sending a user command to the control unit 305 to activate said slave robot 303. According to a mode of operation, said user command is a foot pedal command. According to a mode of operation, said user command is a manual command provided to said master input tool 306.

According to a preferred mode of operation, the step of controlling is carried out by moving said slave robot 303 in response to said master input tool 306 motion. Preferably, this step comprises the further step of moving said surgical instrument 304 of the slave robot 303 in response to said master input tool 306 motion. In other words, controlling the motion of said at least one surgical instrument 304 of the slave robot 303 by handling said master input tool 306. According to a preferred mode of operation, each master input tool 306 controls a single surgical instrument 304 of the slave robot 303. In other words, according to a preferred mode of operation a single surgical instrument 304 is paired along a master-slave pair to one master input tool 306.

According to a mode of operation, said method comprises the further step of deactivating said slave robot 303. In other words, according to a mode of operation, said method comprises the further step of uncoupling said slave robot 303 from said master input tool 306. Preferably, said step is carried out by the control unit 305 either by sending a command signal to the slave robot 303 for the purpose of locking the motion of at least said surgical instrument 304 or by interrupting the communication towards said surgical instrument 304.

According to a preferred mode of operation, said step of uncoupling said slave robot 303 from said master input tool 306 is performed by sending a foot pedal command. For example, said foot pedal command is transmitted by means of a deadman's foot-operated clutch device 345 or the like.

According to a preferred mode of operation, said step of uncoupling said slave robot 303 from said master input tool 306 is automatically carried out when the seating detector 328 detects the surgeon's detachment from the seating surface 310 of the surgical chair 309 for the purpose of standing up. Preferably, said seating detector 328 transmits a command signal to said control unit 305 for the purpose of uncouple said slave robot 303 from said master input tool 306.

According to a preferred mode of operation, said step of uncoupling said slave robot 303 from said master input tool 306 is automatically carried out by the robotic surgery system 301 when the master input tool 306 is detected as being located within said safety tracking volume portion 354. In other words, said step of uncoupling said slave robot 303 from said master input tool 306 is automatically carried out by the robotic surgery system 3 when the master input tool 306 is detected as being located outside said tracking sub-volume 329.

According to a preferred mode of operation, the method comprises the further step of pivoting around a substantially vertical roll axis (V-V) while seating on a seating surface (310) of the surgical chair (309) thereby pivoting around the same substantially vertical roll axis (V-V) the predefined tracking volume (308). In this way, no unwanted command are transmitted to the slave robot during pivoting.

According to a mode of operation, a surgeon 332 performs said method.

By virtue of the features described above, provided either separately or in combination, where applicable, in particular embodiments, it is possible to satisfy the sometimes contrasting needs disclosed above, and to obtain the aforesaid advantages, and in particular:

- it is provided a robotic surgery system, as well as a sterile console, as well an operating arena, that increases the comfort of the surgeon during robotic surgery without for this reason resulting in a reduced precision of detection of input commands;
- the surgeon when performing robotic surgery, as well as robotic microsurgery, can seat close to, and at the same time can move around, the patient anatomy;
- the comfort of the surgeon during surgery is enhanced, and consequently the risk of focus loss is reduced to minimum, also during long-lasting surgical operations on a patient anatomy;
- the surgeon can drop the master input tool in a safe and sterile place reducing the risk to transmit unwanted command to the slave surgical instrument even during pivoting of the chair about a vertical axis;
- the surgeon can see the patient anatomy with the naked eye during surgery, if needed.

Those skilled in art may make many changes and adaptations to the embodiments described above or may replace elements with others which are functionally equivalent in order to satisfy contingent needs without however departing from the scope of the appended claims.

LIST OF REFERENCES

301 Robotic surgery system
302 Sterile console
303 Slave robot assembly, or slave robot
304 Slave surgical instrument, or surgical instrument
305 Control unit
306 Master input tool
306L Left master input tool
306R Right master input tool
307 Field generator
308 Tracking volume
308L First tracking volume
308R Second tracking volume
309 Surgical chair
310 Seating surface of the surgical chair
311 Sensing device of the master input tool
312 Chair wired connection
313 Chair wireless connection
314 Chair base structure
315 Seating lower support portion
316 Seatback portion
317L; R) Armrest assembly (left; right)
318 Armrest surface
319 Armrest adjusting device
320 Armrest element
321 Display
322 Seating adjustment device
323 Ground contacting wheel
324 Tool supporting element or tool holding element
325 Tool receptacle
326 Cup bottom wall
327 Cup lateral wall
328 Seating detector
329 Tracking sub-volume
330 Master wired connection
331 Master wireless connection
332 Surgeon
333 Operating arena
334 Surgical arm
335 Micromanipulator
336 Operating table
337 Patient anatomy
338 Vision assembly
339 Microscope ocular device
340 Image acquisition device
342 Robot cart
343 Cart handle
344 Power supply cable
345 Clutch device
346 Seating element body
347 Lower seating body portion
348 Manual command or user command
349 First command signal
350 Second command signal
351 Cart ground contacting unit
352 Connecting element
353 Telescopically extendable portion
354 Safety tracking volume
355 Ground or soil
356 Surgeon's hand
357 Surgeon's back
358 Remote location
359 Remote screen
360 Remote eyeglasses
361 Sterile drape of the sterile console
362 Wall or barrier
V-V Vertical axis

The invention claimed is:

1. A master console for a robotic surgery system, configured to detect a manual command, the master console comprising:
- at least one master input tool mechanically ungrounded and configured to be hand-held by a surgeon during surgery;
- at least one surgical chair comprising a seating surface to accommodate the surgeon during surgery;
- a tracking system for detecting position and orientation of said at least one master input tool within a predefined tracking volume;
- at least one tool resting element providing a support for said at least one master input tool when the surgeon does not hand-hold said at least one master input tool;
- wherein:
  - said at least one master input tool defines at least one first frame of reference attached thereto;
  - said tracking system comprises a single magnetic field generator defining a second frame of reference attached thereto;
  - said predefined tracking volume is integral with said single magnetic field generator of the tracking system;
  - the position and orientation detected by said tracking system is a position and orientation of said at least one first frame of reference with respect to the second frame of reference, so that a control unit of the robotic surgery system is configured to receive information about said position and orientation of said at least one master input tool within said predefined tracking volume and for transmitting a command signal to a slave robot assembly to actuate at least one surgical instrument;

said single magnetic field generator of the tracking system is fixed relative to a portion of the surgical chair so that, when the surgeon is seated on said seating surface of the surgical chair and holds said at least one master input tool, said at least one master input tool is located within said predefined tracking volume, position and orientation of said at least one master input tool being detectable by the tracking system;

wherein said single magnetic field generator of the tracking system is fixed below said seating surface;

wherein said surgical chair comprises a seating lower support portion fixed to said seating surface and located under said seating surface, said seating lower support portion comprising said single magnetic field generator, and wherein said single magnetic field generator is integral with said seat lower support portion below the seating surface, and said predefined tracking volume is vertically aligned with said seating surface.

2. The master console according to claim 1, further comprising a sterile drape covering said seating surface of the surgical chair.

3. The master console according to claim 1, wherein said surgical chair comprises a seat adjustment device allowing the surgical chair, and the seating lower support portion of the surgical chair, to roll around a substantially vertical roll axis.

4. The master console according to claim 1, wherein said seating surface of the surgical chair is adjustable in height.

5. The master console according to claim 1, wherein said surgical chair is movable in at least one direction substantially co-planar with the seating surface within an operating arena and/or in a direction in a horizontal or sub-horizontal plane.

6. The master console according to claim 1, wherein:

said at least one master input tool is operatively connected to said surgical chair by a tool wired connection; and/or wherein said at least one master input tool has a shape and size of a manual microsurgical instrument, including a needle holder or a tweezer.

7. The master console according to claim 1, wherein said at least one master input tool comprises two master input tools, including a first master input tool and a second master input tool arranged opposite to a substantially vertical roll axis of the seating surface of the surgical chair.

8. The master console according to claim 1, further comprising a footswitch pedal detached from the single magnetic field generator, and said footswitch pedal being detached from the surgical chair.

9. The master console according to claim 1, wherein said single magnetic field generator of the tracking system is directly fixed to said seat lower support portion below said seating surface.

10. The master console according to claim 1, wherein the predefined tracking volume is vertically aligned with an area within a periphery of the seating surface.

11. The master console according to claim 1, wherein:

said surgical chair comprises a chair base structure providing structural support to the seating lower support portion;

said seating lower support portion is pivotable around a substantially vertical roll axis with respect to said chair base structure; and the predefined tracking volume is rotationally fixed with the seating surface of the surgical chair during rolling around the substantially vertical roll axis.

12. The master console according to claim 11, wherein said chair base structure comprises at least one ground contacting wheel.

13. The master console according to claim 12, further comprising a locking device for selectively blocking at least one degree of freedom of motion provided by the at least one ground contacting wheel of the surgical chair.

14. An operating arena comprising:

the master console according to claim 1;

the slave robot assembly comprising the surgical instrument configured to operate on a patient anatomy;

a patient supporting structure located within the operating arena and supporting the patient anatomy during surgery.

15. The operating arena according to claim 14, further comprising a surgery vision assembly showing surgery to the surgeon; wherein said surgery vision assembly comprises at least one image acquisition device, including a microscope acquisition device, configured to acquire real-time images of ongoing surgery, and at least one image showing device, including a display and/or a microscope ocular device.

16. The master console according to claim 1, wherein the seating surface of the surgical chair is pivotable about a substantially vertical roll axis during surgery.

17. The master console according to claim 16, wherein the predefined tracking volume is rotationally fixed with the seating surface of the surgical chair during pivoting of the seating surface around the substantially vertical roll axis during surgery.

* * * * *